United States Patent
Hu et al.

(10) Patent No.: US 9,447,455 B2
(45) Date of Patent: Sep. 20, 2016

(54) METHODS AND COMPOSITIONS FOR THE TARGET-LOCALIZED ANCHORING OF DETECTABLE LABEL

(75) Inventors: Celine Hu, Tiburon, CA (US); Julie Perkins, Sunnyvale, CA (US); Hetian Gao, Fremont, CA (US); Lisen Wang, Sunnyvale, CA (US)

(73) Assignee: Headway Technologies, Inc., Milpitas, CA (US)

( * ) Notice: Subject to any disclaimer, the term of this patent is extended or adjusted under 35 U.S.C. 154(b) by 0 days.

(21) Appl. No.: 13/396,352

(22) Filed: Feb. 14, 2012

(65) Prior Publication Data

US 2012/0289419 A1    Nov. 15, 2012

Related U.S. Application Data

(60) Provisional application No. 61/443,560, filed on Feb. 16, 2011.

(51) Int. Cl.
| C12Q 1/68 | (2006.01) |
| C07D 495/04 | (2006.01) |
| C07D 207/408 | (2006.01) |

(52) U.S. Cl.
CPC ......... *C12Q 1/6816* (2013.01); *C07D 207/408* (2013.01); *C07D 495/04* (2013.01); *C12Q 1/6834* (2013.01)

(58) Field of Classification Search
None
See application file for complete search history.

(56) References Cited

U.S. PATENT DOCUMENTS

| | | | |
|---|---|---|---|
| 4,599,303 A | 7/1986 | Yabusaki et al. | |
| 4,826,967 A | 5/1989 | Glass | |
| 5,028,594 A | 7/1991 | Carson | |
| 5,082,934 A | 1/1992 | Saba et al. | |
| 5,124,246 A | 6/1992 | Urdea et al. | |
| 5,196,306 A | 3/1993 | Bobrow et al. | |
| 5,512,439 A | 4/1996 | Hornes et al. | |
| 5,580,731 A | 12/1996 | Chang et al. | |
| 5,616,464 A | 4/1997 | Albagli et al. | |
| 5,635,352 A | 6/1997 | Urdea et al. | |
| 5,653,859 A | 8/1997 | Parton et al. | |
| 5,767,259 A | 6/1998 | Albagli et al. | |
| 5,981,297 A | 11/1999 | Baselt | |
| 6,004,513 A | 12/1999 | Albagli et al. | |
| 6,005,093 A | 12/1999 | Wood et al. | |
| 6,177,243 B1 | 1/2001 | Albagli et al. | |
| 6,187,532 B1 | 2/2001 | Wood et al. | |
| 6,277,570 B1 | 8/2001 | Wood et al. | |
| 6,303,799 B1 | 10/2001 | Cheng et al. | |
| 6,495,676 B1 | 12/2002 | Wood et al. | |
| 6,573,048 B1 | 6/2003 | Vanatta et al. | |
| 6,590,091 B2 | 7/2003 | Albagli et al. | |
| 6,696,246 B1 | 2/2004 | Huan et al. | |
| 6,737,239 B2 | 5/2004 | Wood et al. | |
| 6,743,639 B1 | 6/2004 | Tondra et al. | |
| 6,800,768 B1 | 10/2004 | Cheng et al. | |
| 6,875,621 B2 | 4/2005 | Tondra | |
| 7,033,758 B2 | 4/2006 | Kenny et al. | |
| 7,163,788 B2 | 1/2007 | Tong et al. | |
| 7,223,833 B1 | 5/2007 | Nielsen et al. | |
| 7,332,355 B2 | 2/2008 | Hsieh-Wilson et al. | |
| 2001/0012616 A1 | 8/2001 | Wood et al. | |
| 2002/0051971 A1 | 5/2002 | Stuelpnagel et al. | |
| 2002/0102578 A1* | 8/2002 | Dickinson et al. | 435/6 |
| 2002/0127574 A1 | 9/2002 | Mirkin et al. | |
| 2002/0177157 A1 | 11/2002 | Luo et al. | |
| 2003/0148282 A1 | 8/2003 | Mirkin et al. | |
| 2003/0166177 A1 | 9/2003 | Dordick et al. | |
| 2005/0100930 A1 | 5/2005 | Wang et al. | |
| 2006/0177850 A1 | 8/2006 | Schermer et al. | |
| 2006/0252085 A1 | 11/2006 | Pollner et al. | |
| 2006/0286583 A1 | 12/2006 | Luo et al. | |
| 2007/0117151 A1 | 5/2007 | Frederix et al. | |
| 2007/0184436 A1 | 8/2007 | Myerson et al. | |
| 2007/0202576 A1 | 8/2007 | Bodepudi et al. | |
| 2008/0038725 A1 | 2/2008 | Luo et al. | |
| 2008/0220979 A1 | 9/2008 | Wang et al. | |
| 2009/0048123 A1* | 2/2009 | Medintz et al. | 506/15 |
| 2009/0104707 A1 | 4/2009 | Wang et al. | |
| 2009/0111709 A1* | 4/2009 | Burke et al. | 506/9 |
| 2010/0129819 A1 | 5/2010 | Hu et al. | |
| 2010/0130383 A1 | 5/2010 | Hu et al. | |
| 2011/0059444 A1 | 3/2011 | Stromberg et al. | |

FOREIGN PATENT DOCUMENTS

| JP | 2006-191932 A | 7/2006 |
|---|---|---|
| JP | 2007-189991 A | 8/2007 |
| JP | 2007-225586 A | 9/2007 |
| WO | WO 9011523 | 10/1990 |
| WO | 95/16055 A1 | 6/1995 |
| WO | 97/27317 A1 | 7/1997 |
| WO | 03/083440 A2 | 10/2003 |
| WO | WO 03083440 | 10/2003 |
| WO | 2005/033343 A2 | 4/2005 |
| WO | 2006124771 | 11/2006 |
| WO | WO 2007005626 | 1/2007 |
| WO | 2007056250 | 5/2007 |
| WO | WO 2008052775 | 5/2008 |
| WO | WO 2008101024 | 8/2008 |
| WO | 2009112498 | 9/2009 |

OTHER PUBLICATIONS

Martins, V.C., et al., "Femtomolar limit of detection with a magnetoresistive biochip," 2009, Biosensors and Bioelectronics, 24, pp. 2690-2695.*

(Continued)

*Primary Examiner* — Christopher M Gross

(74) *Attorney, Agent, or Firm* — Michael B. Rubin; Bozicevic, Field & Francis LLP

(57) ABSTRACT

Highly reactive functionalized substrates and linker molecules for use in the detection of molecular targets and other analytes of interest are provided as are kits, reaction mixtures and methods utilizing the same.

37 Claims, 14 Drawing Sheets

(56) References Cited

OTHER PUBLICATIONS

Joshi, Neel et al., "A Three-Component Mannich Type Reaction for Selective Tyrosine Bioconjugation," Nov. 19, 2004, J. Am. Chem. Soc., 126, pp. 15942-15943.*
Invitrogen Tyramide Signal Amplification Kit flyer (2005).*
Gryaznov et al (1993 JACS 115:3808-9).*
Gramlich et al. (2008) "Postsynthetic DNA Modification through the Copper-Catalyzed Azide-Alkyne Cycloaddition Reaction" Angew Chem Int Ed 47:8350-8358.
Baselt et al., A biosensor based on magnetoresistance technology. Biosens. Bioelectron. 1998;13(7-8):731-9.
Baskin et al., Copper-free click chemistry for dynamic in vivo imaging. Proc. Natl. Acad. Sci. USA 2007;104(43):16793-7.
Bird et al., Single-chain antigen-binding proteins. Science 1988;242:423-6.
Casey, 2005 Nobel Prize in Chemistry: Development of the olefin metathesis method in organic synthesis. J. Chem. Edu. 2006;83(2):192-5.
Chan et al., Polytriazoles as copper(I)-stabilizing ligands in catalysis. Org. Lett. 2004;6(17):2853-5.
Chavali et al., Oligonucleotide properties determination and primer designing: a critical examination of predictions. Bioinformatics 2005;21(20):3918-25.
Collins, et al., A branched DNA signal amplification assay for quantification of nucleic acid targets below 100 molecules/ml., Nucleic Acids Res. Aug. 1, 1997; 25(15): 2979-2984.
Donnelly et al., 'Click' cycloaddition catalysts: copper(I) and copper(II) tris(triazolylmethyl)amine complexes. Chem. Commun. 2008:2459-61.
Drake et al., Gd-doped iron-oxide nanoparticles for tumour therapy via magnetic field hyperthermia. J. Mater. Chem. 2007;17:4914-8.
Ebright et al., Conversion of a helix-turn-helix motif sequence-specific DNA binding protein into a site-specfic DNA cleavage agent. Proc. Natl. Acad. Sci. USA 1990;87:2882-6.
Edelstein et al., The BARC biosensor applied to the detection of biological warfare agents. Biosens. Bioelectron. 2000;14:pp. 805-813.
Ferreira et al., Biodetection using magnetically labeled biomolecules and arrays of spin valve sensors (invited). J. Appl. Phys. 2003;93(10):7281-6.
Ferreira et al., Effect of spin-valve sensor magnetostatic fields on nanobead detection for biochip applications. J Appl. Phys. 2005;97(10Q904):1-3.
Graham et al., Single magnetic microsphere placement and detection on-chip using current line designs with integrated spin valve sensors: Biotechnological applications. J. Appl. Phys. 2002;91(10):7786-8.
He et al., Empirical establishment of oligonucleotide probe design criteria. Appl. Env. Microbiol. 2005;71(7):3753-60.
Himo et al., Copper(I)-catalyzed synthesis of azoles. DFT study predicts unprecedented reactivity with intermediates. J. Amer. Chem. Soc. 2005;127:210-6.
Hunkapiller et al., The growing immunoglobulin gene superfamily. Nature 1986;323:15-6.
Huston et al., Protein engineering of antibody binding sites: Recovery of specific activity in an anti-digoxin single-chain Fv analogue produced in *Escherichia coli*. Proc. Natl. Acad. Sci. USA 1988;85:5879-83.
IBM Almaden Research Center, Magnetic Tunnel Junctions (MTJs) (2006).
Ito et al., Development of an artificial antibody system with multiple valency using an Fv fragment fused to a fragment of protein A. J. Biol. Chem. 1993;268(27):20668-75.
Kim et al., Site-specific gene modification by PNAs conjugated to psoralen. Biochemistry 2006;45:314-23.
Kocalka et al., Rapid and efficient DNA strand cross-linking by click chemistry. Chembiochem 2008;9:1280-5.
Kolb et al., The growing impact of click chemistry on drug discovery. Drug Discovery Today 2003;8(24):1128-37.

Krasia et al., Formation of oligotriazoles catalysed by cucurbituril. Chem. Commun. 2002:22-23.
Lanzavecchia et al., The use of hybrid hybridomas to target human cytotoxic T lymphocytes. Eur. J. Immunol. 1987;17:105-11.
Lewis et al., Discovery and characterization of catalysts for azide-alkyne cycloaddition by fluorescence quenching. J. Am. Chem. Soc. 2004;126:9152-3.
Li et al., Detection of single micron-sized magnetic bead and magnetic nanoparticles using spin valve sensors for biological applications. J. Appl. Phys. 2003;93(10):7557-9.
Li et al., Model and experiment of detecting multiple magnetic nanoparticles as biomolecular labels by spin valve sensors. IEEE Trans. Magn., 2004;40:3000-2.
Li et al., Selection of optimal oligonucleotide probes for microarrays using multiple criteria, global alignment and parameter estimation. Nucleic Acids Research 2005;33(19):6114-23.
Lin et al., Mechanistic investigation of the Staudinger ligation. J. Am. Chem. Soc. 2005;127:2686-95.
Long et al., Localized "click" chemistry through dip-pen nanolithography. Adv. Mat. 2007;19:4471-3.
Luo et al., Controlled assembly of dendrimer-like DNA. Nature Materials 2004;3:38-42.
Lynn et al., Water-soluble ruthenium alkylidenes: Synthesis, characterization, and application to olefin metathesis in protic solvents. J. Am. Chem. Soc. 2000;122: 6601-9.
Miller et al., A DNA array sensor utilizing magnetic microbeads and magnetoelectronic detection. J. Magn. Magn. Mater., 2001;225:138-44.
Mottes et al., Restoration by T4 ligase of DNA sequences sensitive to "flush"-cleaving restriction enzyme. Nucleic Acids Research 1977;4(7):2467-76.
Nagasaki et al., Photoenhancement of transfection efficiency using novel cationic lipids having a photocleavable spacer. Bioconjugate Chem. 2003;14:513-6.
Okamoto et al., Synthesis and properties of peptide nucleic acids containing a psoralen unit. Org. Lett. 2001;3(6):925-7.
Park, et al., Array-Based Electrical Detection of DNA with Nanoparticle Probes, Science Feb. 22, 2002: vol. 295. No. 5559, pp. 1503-1506.
Pendergrast et al., Determination of the orientation of a DNA binding motif in a protein-DNA complex by photocrosslinking. Proc. Nati. Acad. Sci. USA 1992;89:10287-91.
Praseuth et al., Double helices with parallel strands are formed by nuclease-resistant oligo-[α]-deoxynucleotides and oligo-[α]-deoxynucleotides covalently linked to an intercalating agent with complementary oligo-[β]-deoxynucleotides. J. Mol. Biol. 1987;196:939-42.
Praseuth et al., Sequence-specific binding and photocrosslinking of α and β oligodeoxynucleotides to the major groove of DNA via triple-helix formation. Proc. Natl. Acad. Sci. USA 1988;85:1349-53.
Rodionov et al., Mechanism of the ligand-free Cu(I)-catalyzed azide-alkyne cycloaddition reaction. Angrew. Chem. Int. Ed. 2005;44:2210-5.
Rostovtsev et al., A stepqise Huisgen cycloaddition process: Copper(I)-catalyzed regioselective "ligation" of azides and terminal alkynes. Angew. Chem. Int. Ed. 2002;41(14):2596-9.
Ruparel et al., Design and synthesis of a 3'-O-allyl photocleavable fluorescent nucleotide as a reversible terminator for DNA sequencing by synthesis. Proc. Natl. Acad. Sci. 2006;102(17):5932-7.
Saffran et al., Preparation and characterization of biotinylated psoralen. Nucleic Acids Research 1988;16(15):7221-31.
Salic et al., A chemical method for fast and sensitive detection of DNA synthesis in vivo. Proc. Natl. Acad. Sci. 2008;105(7):2415-20.
Saravis et al., Amplified immunoperoxidase staining of isoelectrically focused human tumor markers. Elecrophoresis 1980;1:191-3.
Saxon et al., Cell surface engineering by a modified Staudinger reaction. Science 2000;287(5460):2007-10.
Schrag et al., Magnetic tunnel junction sensor development for industrial applications. Micro Magnetics, Inc. (2006).
Seol et al., Gold nanoparticles: enhanced optical trapping and sensitivity coupled with significant heating. Optics Letters 2006;31(16):2429-31.

(56) References Cited

OTHER PUBLICATIONS

Shchepinov et al., Oligonucleotide dendrimers: stable nano-structures. Nucleic Acids Research 1999;27(15):3035-41.

Shchepinov et al., Oligonucleotide dendrimers: synthesis and sue as polylabelled DNA probes. Nucleic Acids Research 1997;25(22):4447-54.

Shen et al., In situ detection of single micron-sized magnetic beads using magnetic tunnel junction sensors. Appl. Phys. Lett., 2005;86:253901(1-3).

Speel et al., Amplification methods to increase the sensitivity of in situ hybridization: Play Card(S). J. Hist. Cyt. 1999;47(3):281-8.

Spielmann et al., DNA structural reorganization upon conversion of a psoralen furan-side monoadduct to an interstrand cross-link: Implications for DNA repair. Proc. Natl. Acad. Sci. USA 1995;92:2345-9.

Sugino et al, Interaction of bacteriophage T4 RNA and DNA ligases in joining of duplex DNA at base-paired ends. J. Biol. Chem. 1977;252(11):3987-94.

Tornoe et al., Peptidotriazoles on solid phase: [1,2,3]-Triazoles by regiospecific copper(I)catalyzed 1,3-dipolar cycloadditions of terminal alkynes to azides. J. Org. Chem. 2002;67:3057-64.

Van De Sande et al., T4 polynucleotide ligase catalyzed joining of short synthetic DNA duplexes at base-paired ends. Biochemistry 1978;17(4):723-9.

Wang et al., Bioconjugation by copper(I)-catalyzed azide-alkyne [3+2] cycloaddition. J. Am. Chem. Soc. 2003;125: 3192-3.

Wang et al., Towards a magnetic microarray for sensitive diagnostics. J. Magn. Magn. Mater. 2005;293:731-6.

Wilson et al. "A multiplexed PCR-coupled liquid bead array for the simultaneous detection of four biothreat agents" Molecular and Cellular Probes 19(2):137 (2005).

Wittung et al., Interactions of DNA binding ligands with PNA-DNA hybrids. Nucleic Acids Research 1994;22(24):5371-7.

Wu et al., Efficiency and fidelity in a click-chemistry route to triazole dendrimers by the copper(I)-catalyzed ligation of azides and alkynes. Angrew. Chem. Int. Ed. 2004;43:3928-32.

Yoo et al., Copper-catalyzed synthesis of N-sulfonyl-1,2,3-triazoles: Controlling selectivity. Angew. Chem. Int. Ed. 2007;46:1730-3.

Invitrogen by Life Technologies; "Dynabeads ® M-280 Streptavidin"; Catalog Nos. 11205D, 11206D, 60210; Oct. 2011; 2 pages.

Graham et al. (2004) "Magnetoresistive-Based Biosensors and Biochips" TRENDS Biotechnol 22(9):455-462.

Lai et al. (1999) "Rapid, Femtomolar Bioassays in Complex Matrices Combining Microfluidics and Magnetoelectronics" Biosens Bioelectron 23(2):191-200.

Mulvaney et al. (2007) "Nucleic Acid-Based Cross-Linking Assay for Detection and Quantification of Hepatitis B Virus DNA" J Clin Microbiol 37(1):161-164.

Webb; Thomas R., et al.; "Sequence-Specific Cross-Linking of Deoxyoligonucleotides via Hybridization-Triggered Alkylation"; J. Am. Chem. Soc. 108; (1986); pp. 2764-2765.

* cited by examiner

Figure 6
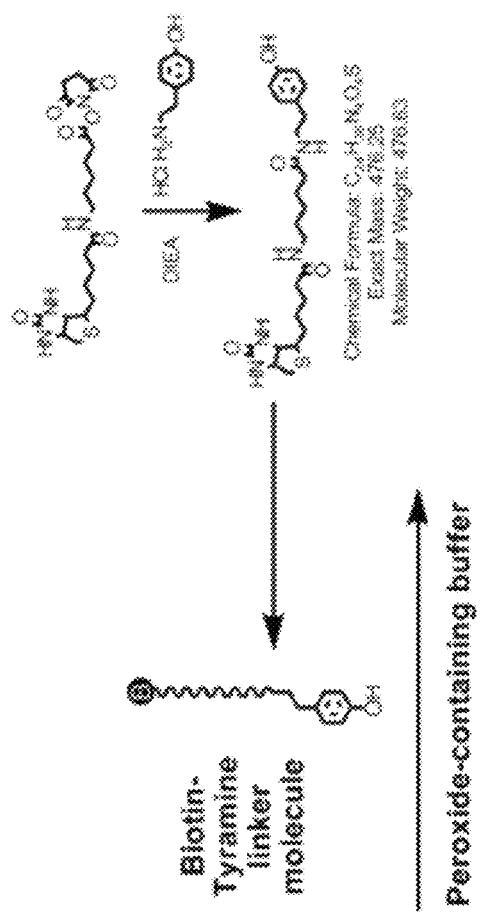
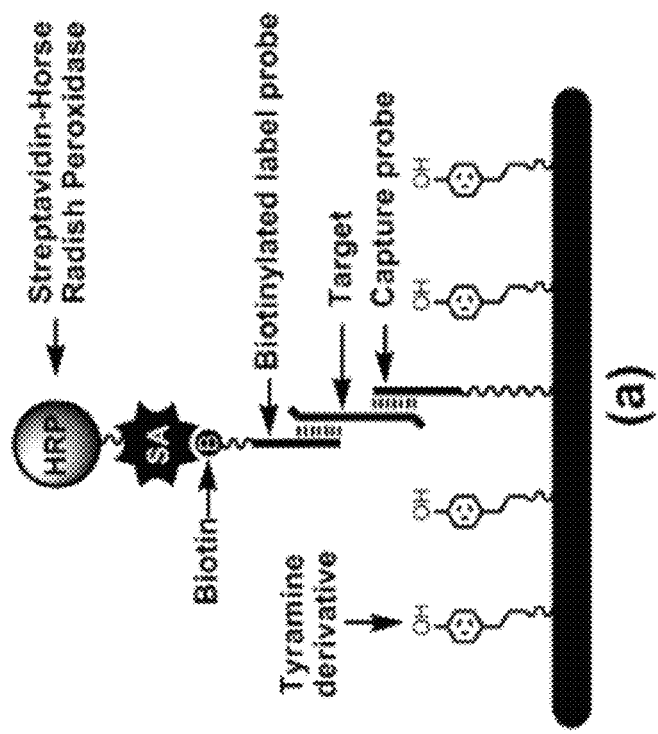

Figure 7
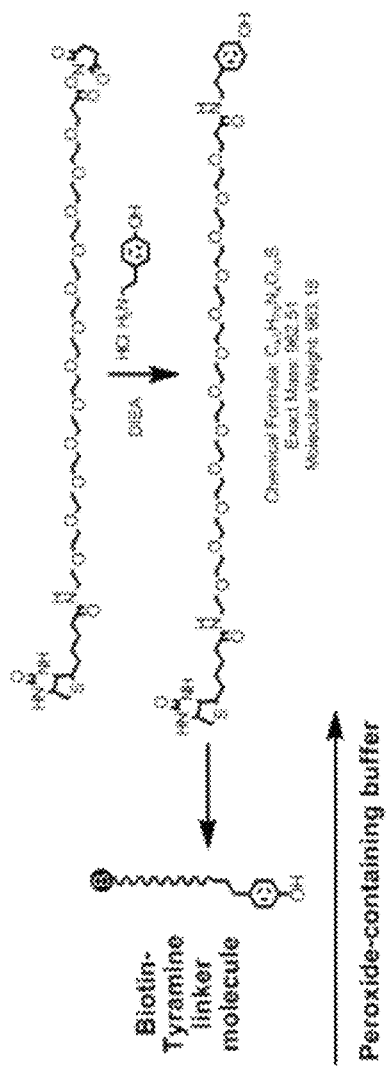
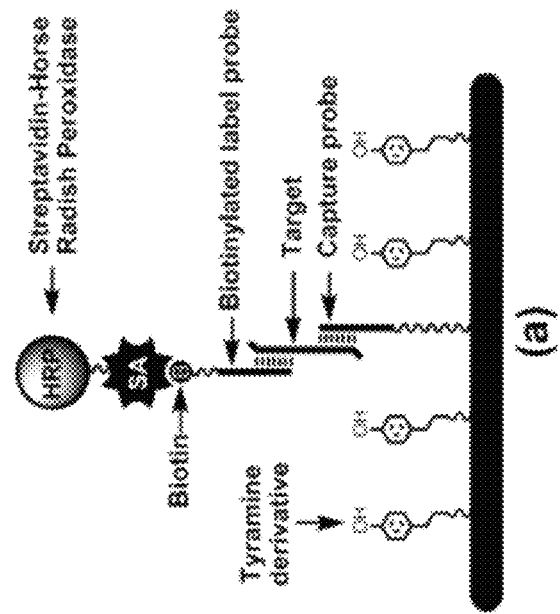

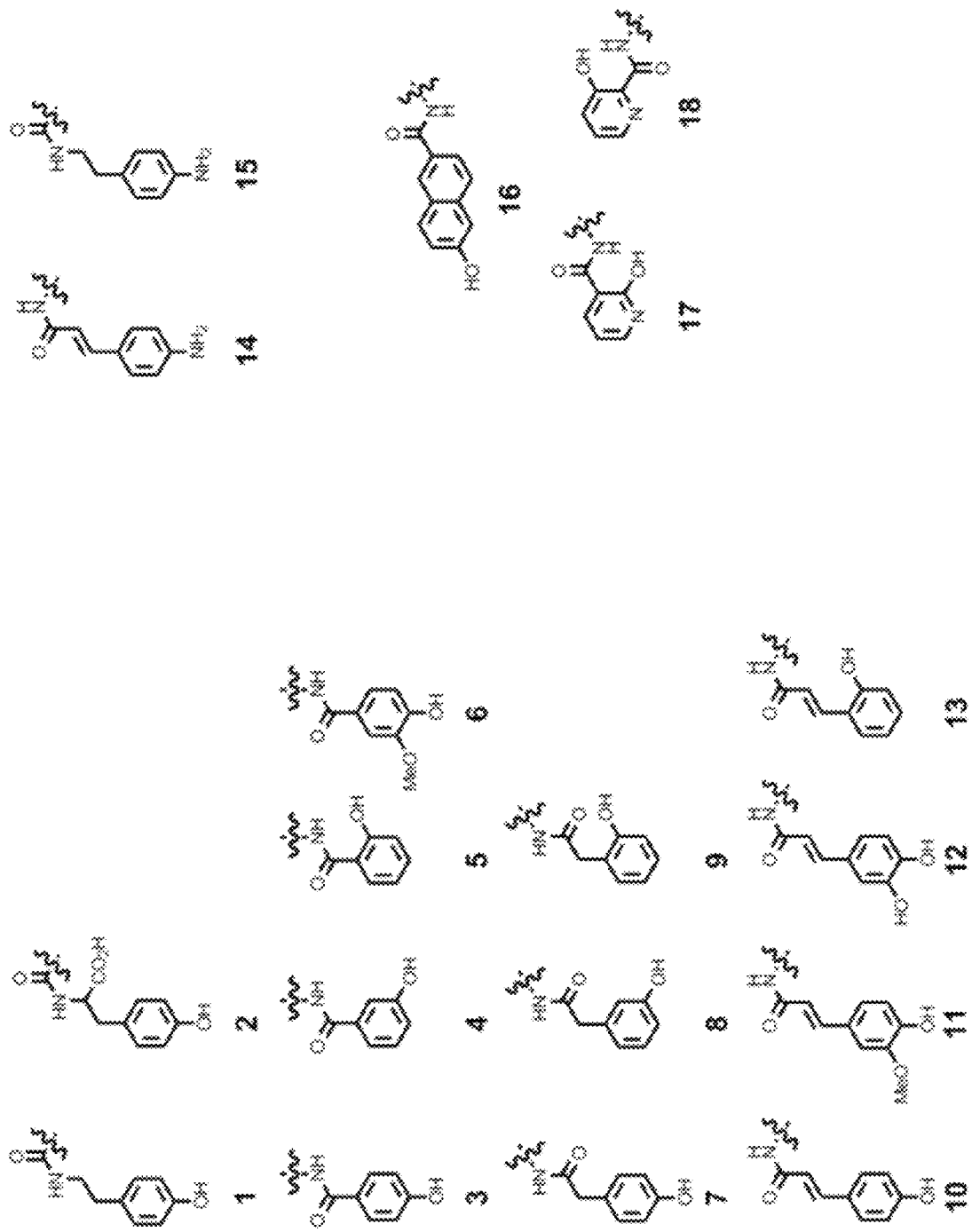

METHODS AND COMPOSITIONS FOR THE TARGET-LOCALIZED ANCHORING OF DETECTABLE LABEL

CROSS-REFERENCE TO RELATED APPLICATION

This application claims priority to U.S. Provisional Patent Application No. 61/443,560, filed on Feb. 16, 2011, which is incorporated by reference herein in its entirety and for all purposes.

BACKGROUND

Many of the current methods for the detection of biomolecules rely on the use of fluorescent dyes applied as labels for the biomolecules. Without using high cost instruments with large footprints, at least a few thousand fluorescent dye molecules are generally required for detection. Other techniques utilize magnetic sensor arrays to detect biomolecules with magnetic particles utilized as labels. These approaches utilize the sensitive magnetic sensors similar to those in computer hard disc drives. There are, however, technical issues which limit the ability of the currently available methods to detect biomolecules with high sensitivity. For example, there may be a large discrepancy between the size and mass of the biomolecules relative to the labels used for detection which makes it difficult to anchor the labels to a substrate surface for detection. The present disclosure addresses these issues and provides related advantages.

SUMMARY OF THE INVENTION

Highly reactive functionalized substrates and linker molecules for use in the detection of molecular targets and other analytes of interest are provided as are kits, reaction mixtures and methods utilizing the same.

In a first aspect, the present disclosure provides a functionalized substrate including: a supporting material; one or more target-specific capture probes bound to the surface of the supporting material; and a plurality of synthetic, non-naturally occurring molecules bound to the surface of the supporting material; wherein each of the synthetic non-naturally occurring molecules includes aromatic covalent bond-forming reactive groups present at a concentration greater than that found in naturally occurring proteins or nucleic acids.

In one embodiment of the first aspect, an aromatic covalent bond-forming reactive group of the aromatic covalent bond-forming reactive groups is positioned at an exposed terminus of one of the synthetic, non-naturally occurring molecules.

In one embodiment of the first aspect, the synthetic, non-naturally occurring molecules contain neither tyrosine nor thymine.

In one embodiment of the first aspect, the functionalized substrate includes a greater number of covalent bond-forming reactive groups per unit area than found in naturally occurring proteins or tissues.

In one embodiment of the first aspect, each of the synthetic, non-naturally occurring molecules includes a covalent bond-forming reactive group having greater reactivity than a covalent bond-forming reactive group of a naturally occurring protein or nucleic acid.

In one embodiment of the first aspect, each of the synthetic, non-naturally occurring molecules includes a covalent bond-forming reactive group having greater reactivity than thymine and tyrosine.

In one embodiment of the first aspect, the supporting material includes silicon.

In one embodiment of the first aspect, each of the synthetic, non-naturally occurring molecules includes a dendrimer structure.

In one embodiment of the first aspect, each of the synthetic, non-naturally occurring molecules includes a tyrosine amino acid.

In one embodiment of the first aspect, each of the synthetic, non-naturally occurring molecules includes a phenol-carboxylic acid copolymer.

In one embodiment of the first aspect, wherein each of the synthetic, non-naturally occurring molecules includes phenol and amino groups.

In one embodiment of the first aspect, each of the synthetic, non-naturally occurring molecules includes lysine and tyrosine amino acids.

In one embodiment of the first aspect, each of the synthetic, non-naturally occurring molecules includes tyramine or a tyramine derivative.

In one embodiment of the first aspect, each of the synthetic, non-naturally occurring molecules includes thymine or a thymine derivative.

In one embodiment of the first aspect, the synthetic, non-naturally occurring molecules are polypeptides including covalent bond-forming reactive groups present at a concentration greater than that found in naturally occurring proteins.

In one embodiment of the first aspect, the synthetic, non-naturally occurring molecules are oligonucleotides including covalent bond-forming reactive groups present at a concentration greater than that found in naturally occurring oligonucleotides.

In one embodiment of the first aspect, the functionalized substrate includes a plurality of the target-specific capture probes, wherein the target-specific capture probes are oligonucleotides.

In one embodiment of the first aspect, the functionalized substrate includes a plurality of the target-specific capture probes, wherein the target-specific capture probes are polypeptides. In one such embodiment, the polypeptides are antibodies or fragments thereof.

In a second aspect, the present disclosure provides a detectable label particle, including: a surface functionalized with a plurality of synthetic, non-naturally occurring molecules bound to the surface of the supporting material; wherein each of the synthetic non-naturally occurring molecules includes aromatic covalent bond-forming reactive groups present at a concentration greater than that found in naturally occurring proteins or nucleic acids.

In one embodiment of the second aspect, an aromatic covalent bond-forming reactive group of the aromatic covalent bond-forming reactive groups is positioned at an exposed terminus of one of the synthetic, non-naturally occurring molecules.

In one embodiment of the second aspect, the synthetic, non-naturally occurring molecules contain neither tyrosine nor thymine.

In one embodiment of the second aspect, the functionalized substrate includes a greater number of covalent bond-forming reactive groups per unit area than found in naturally occurring proteins or tissues.

In one embodiment of the second aspect, each of the synthetic, non-naturally occurring molecules includes a covalent bond-forming reactive group having greater reactivity than a covalent bond-forming reactive group of a naturally occurring protein or nucleic acid.

In one embodiment of the second aspect, each of the synthetic, non-naturally occurring molecules includes a covalent bond-forming reactive group having greater reactivity than thymine and tyrosine.

In one embodiment of the second aspect, each of the synthetic, non-naturally occurring molecules includes a dendrimer structure.

In one embodiment of the second aspect, each of the synthetic, non-naturally occurring molecules, includes a tyrosine amino acid.

In one embodiment of the second aspect, each of the synthetic, non-naturally occurring molecules includes a phenol-carboxylic acid copolymer.

In one embodiment of the second aspect, each of the synthetic, non-naturally occurring molecules include phenol and amino groups.

In one embodiment of the second aspect, each of the synthetic, non-naturally occurring molecules includes lysine and tyrosine amino acids.

In one embodiment of the second aspect, each of the synthetic, non-naturally occurring molecules includes tyramine or a tyramine derivative.

In one embodiment of the second aspect, each of the synthetic, non-naturally occurring molecules includes thymine or a thymine derivative.

In one embodiment of the second aspect, the synthetic, non-naturally occurring molecules are polypeptides including covalent bond-forming reactive groups present at a concentration greater than that found in naturally occurring proteins.

In one embodiment of the second aspect, the synthetic, non-naturally occurring molecules are oligonucleotides including covalent bond-forming reactive groups present at a concentration greater than that found in naturally occurring oligonucleotides.

In one embodiment of the second aspect, the particle includes a magnetic material.

In a third aspect, the present disclosure provides a kit including the functionalized substrate of any one of the embodiments described above in packaged combination with instructions for use with the same.

In one embodiment of the third aspect, the kit further includes a plurality of detectable label particles, wherein each detectable label particle of the plurality is functionalized with a plurality of molecules bound to the surface of the detectable label particle to provide a functionalized detectable label particle, wherein each of the plurality of molecules bound to the surface of the detectable label particle includes a covalent bond forming reactive group.

In one embodiment of the third aspect, the kit further includes a plurality of linker molecules, wherein each linker molecule in the plurality of linker molecules includes a covalent bond-forming reactive group. In one such embodiment, the kit further includes a plurality of detectable label particles wherein each detectable label particle of the plurality is functionalized with a plurality of molecules bound to the surface of the detectable label particle to provide a functionalized detectable label particle, wherein each of the molecules bound to the surface of the detectable label particle includes a binding moiety configured to bind one or more of the linker molecules. The binding moiety may be configured to bind one or more of the linker molecules non-covalently. In one embodiment, the binding moiety is biotin or streptavidin. In one embodiment, where the binding moiety is streptavidin, the linker molecules include biotin. In an alternative embodiment, where the binding moiety is biotin, the linker molecules include streptavidin.

In one embodiment of the third aspect, the kit further includes a plurality of detectable label particles wherein each detectable label particle of the plurality is functionalized with a plurality of molecules bound to the surface of the detectable label particle to provide a functionalized detectable label particle, wherein each of the molecules bound to the surface of the detectable label particle includes a binding moiety configured to bind one or more of the linker molecules, and wherein the functionalized detectable label particles are functionalized magnetic beads. In one such embodiment, the functionalized magnetic beads have a diameter of about 100 nm to about 1 µm. In another embodiment, the functionalized magnetic beads have a diameter of about 1 µm or greater.

In a fourth aspect, the present disclosure provides a reaction mixture including: (a) a functionalized substrate including a supporting material, one or more target-specific capture probes bound to the surface of the supporting material, and a plurality of synthetic, non-naturally occurring molecules bound to the surface of the supporting material wherein each of the synthetic, non-naturally occurring molecules includes a first covalent bond-forming reactive group; and (b) a plurality of functionalized detectable label particles, wherein each of the functionalized detectable label particles includes a plurality of molecules bound to the surface of a detectable label particle to provide the functionalized detectable label particle, and wherein each of the plurality of molecules bound to the surface of the detectable label particle includes a second covalent bond forming reactive group.

In one embodiment of the fourth aspect, the reaction mixture further includes a target molecule specifically bound to one of the one or more target-specific capture probes. In one such embodiment, the reaction mixture further includes a label probe specifically bound to the target molecule. In one such embodiment, the reaction mixture further includes an enzyme conjugate specifically bound to the label probe. In one such embodiment, a functionalized detectable label particle of the plurality of functionalized detectable label particles is linked via multiple covalent bonds to the surface of the supporting material, in proximity to the target molecule specifically bound to one of the one or more target-specific capture probes, via interaction of the first covalent bond forming reactive groups with the second covalent bond forming reactive groups. In one such embodiment, the reaction mixture includes a plurality of spatially separated, individually detectable target loci.

In one embodiment, where the functionalized detectable label particle of the plurality of functionalized detectable label particles is linked via multiple covalent bonds to the surface of the supporting material, in proximity to the target molecule specifically bound to one of the one or more target-specific capture probes, via interaction of the first covalent bond forming reactive groups with the second covalent bond forming reactive groups, the target molecules are present in the reaction mixture at a concentration of less than about 100 fM.

In another embodiment, where the functionalized detectable label particle of the plurality of functionalized detectable label particles is linked via multiple covalent bonds to the surface of the supporting material, in proximity to the target molecule specifically bound to one of the one or more target-specific capture probes, via interaction of the first covalent bond forming reactive groups with the second covalent bond forming reactive groups, the target molecules are present in the reaction mixture at a concentration of about 0.1 fM to about 100 fM.

In a fifth aspect, the present disclosure provides a reaction mixture including: (a) a functionalized substrate including a supporting material, one or more target-specific capture probes bound to the surface of the supporting material, and a plurality of synthetic, non-naturally occurring molecules bound to the surface of the supporting material wherein each of the synthetic, non-naturally occurring molecules includes a first covalent bond-forming reactive group; (b) a plurality of functionalized detectable label particles, wherein each of the plurality of functionalized detectable label particles includes a plurality of molecules bound to the surface of a detectable label particle to provide a functionalized detectable label particle, and wherein each of the plurality of molecules bound to the surface of the detectable label particle includes a member of a specific binding pair; and (c) a plurality of linker molecules wherein each linker molecule in the plurality of linker molecules is configured to bind one of the plurality of molecules bound to the surface of the functionalized detectable label, and wherein each linker molecule includes a plurality of second covalent bond-forming reactive groups.

In one embodiment of the fifth aspect, the reaction mixture further includes a target molecule specifically bound to one of the one or more target-specific capture probes. In one such embodiment, the reaction mixture further includes a label probe specifically bound to the target molecule. In one such embodiment, the reaction mixture further includes an enzyme conjugate specifically bound to the label probe. In one such embodiment, a functionalized detectable label particle of the plurality of functionalized detectable label particles is bound to multiple linker molecules of the plurality of linker molecules which linker molecules are bound, via covalent bonds between the first covalent bond forming reactive groups and the second covalent bond forming reactive groups, to the surface of the supporting material, in proximity to the bound target molecule. In one such embodiment, the reaction mixture includes a plurality of spatially separated, individually detectable target loci.

In one embodiment; where the functionalized detectable label particle of the plurality of functionalized detectable label particles is linked via multiple covalent bonds to the surface of the supporting material, in proximity to the target molecule specifically bound to one of the one or more target-specific capture probes, via interaction of the first covalent bond forming reactive groups with the second covalent bond forming reactive groups; the target molecules are present in the reaction mixture at a concentration of less than about 100 fM.

In another embodiment, where the functionalized detectable label particle of the plurality of functionalized detectable label particles is linked via multiple covalent bonds to the surface of the supporting material, in proximity to the target molecule specifically bound to one of the one or more target-specific capture probes, via interaction of the first covalent bond forming reactive groups with the second covalent bond forming reactive groups; the target molecules are present in the reaction mixture at a concentration of about 0.1 fM to about 100 fM.

In any of the reaction mixtures described above for the fourth and fifth aspects, the functionalized detectable label particles may be functionalized magnetic beads. In such embodiments, the functionalized magnetic beads may have a diameter of about 100 nm to about 1 μm. In some embodiments, the functionalized magnetic beads have a diameter of about 1 μm or greater.

In any of the reaction mixtures described above for the fourth and fifth aspects, the supporting material may include silicon.

In any of the reaction mixtures described above for the fourth and fifth aspects, each of the synthetic, non-naturally occurring molecules may include a dendrimer structure.

In any of the reaction mixtures described above for the fourth and fifth aspects, each of the synthetic, non-naturally occurring molecules may include a tyrosine amino acid.

In any of the reaction mixtures described above for the fourth and fifth aspects, each of the synthetic, non-naturally occurring molecules may include a phenol-acid copolymer.

In any of the reaction mixtures described above for the fourth and fifth aspects, each of the synthetic, non-naturally occurring molecules may include lysine and tyrosine amino acids.

In any of the reaction mixtures described above for the fourth and fifth aspects, each of the synthetic, non-naturally occurring molecules may include tyramine or a tyramine derivative.

In any of the reaction mixtures described above for the fourth and fifth aspects, each of the synthetic, non-naturally occurring molecules may include thymine or a thymine derivative.

In a sixth aspect, the present disclosure provides a method of indirectly detecting a target molecule immobilized on a substrate surface, including: combining in a reaction mixture (a) a functionalized substrate including a supporting material, one or more target-specific capture probes bound to the surface of the supporting material, and a plurality of synthetic, non-naturally occurring molecules bound to the surface of the supporting material, wherein each of the synthetic, non-naturally occurring molecules includes a first covalent bond-forming reactive group, (b) a plurality of functionalized detectable label particles, each member of the plurality including a plurality of second covalent bond-forming reactive groups, (c) a sample suspected of containing a target molecule, (d) a target-specific label probe, and (e) an enzyme conjugate configured to specifically bind the target-specific label probe and catalyze the formation of covalent bonds between the first covalent bond-forming reactive groups and the second covalent bond-forming reactive groups; and detecting the presence or absence of the functionalized detectable label particles bound to the functionalized surface, wherein the presence of the functionalized detectable label particles indicates the presence of the target molecule immobilized on the functionalized substrate.

In one embodiment of the sixth aspect, the sample suspected of containing the target molecule contains the target molecule at a concentration of less than about 100 fM.

In one embodiment of the sixth aspect, the sample suspected of containing the target molecule contains the target molecule at a concentration of about 0.1 fM to about 100 fM.

In a seventh aspect, the present disclosure provides a method of indirectly detecting a target molecule immobilized on a substrate surface, including: combining in a reaction mixture (a) a functionalized substrate including a supporting material, one or more target-specific capture probes bound to the surface of the supporting material, and a plurality of synthetic, non-naturally occurring molecules bound to the surface of the supporting material, wherein each of the synthetic, non-naturally occurring molecules includes a first covalent bond-forming reactive group, (b) a plurality of functionalized detectable label particles, each member of the plurality of functionalized detectable label particles including a first binding moiety, (c) a plurality of linking molecules, each member of the plurality of linking molecules including a second binding moiety configured to specifically bind the first binding moiety, and a plurality of second covalent bond-forming reactive groups, (d) a sample suspected of containing a target molecule, (e) a target-specific label probe, and (f) an enzyme conjugate configured to specifically bind the target-specific label probe and catalyze the formation of covalent bonds between the first covalent bond-forming reactive groups and the second covalent bond-forming reactive groups; and detecting the presence or absence of the functionalized detectable label particles bound to the functionalized surface, wherein the presence of the functionalized detectable label particles indicates the presence of the target molecule immobilized on the functionalized substrate.

In one embodiment of the seventh aspect, the sample suspected of containing the target molecule contains the target molecule at a concentration of less than about 100 fM.

In one embodiment of the seventh aspect, the sample suspected of containing the target molecule contains the target molecule at a concentration of about 0.1 fM to about 100 fM.

It should be noted that two or more of the embodiments described herein may be combined to produce one or more additional embodiments which include the combined features of the individual embodiments.

BRIEF DESCRIPTION OF THE DRAWINGS

FIG. 6 shows an example of a synthetic scheme for a linker molecule to enable the HRP-mediated deposition of multiple biotin moieties in the vicinity of an immobilized target molecule. The linker molecule includes a biotin moiety and a phenolic group separated by a spacer. The depicted biotinylation reagent includes a N-hydroxyl succinimide (NHS) ester, which reacts readily with tyramine to yield the linker molecule.

FIG. 7 shows an example of a synthetic scheme for a linker molecule to enable the HRP-mediated deposition of multiple biotin moieties in the vicinity of an immobilized target molecule. The linker molecule includes a biotin moiety and a phenolic group separated by a spacer longer than the one shown in FIG. 6. The depicted biotinylation reagent includes a NHS ester, which reacts readily with tyramine to yield the linker molecule.

FIG. 14(1-18) shows chemical structures for the aromatic ring portions of eighteen linker molecules.

DEFINITIONS

Figure 1:
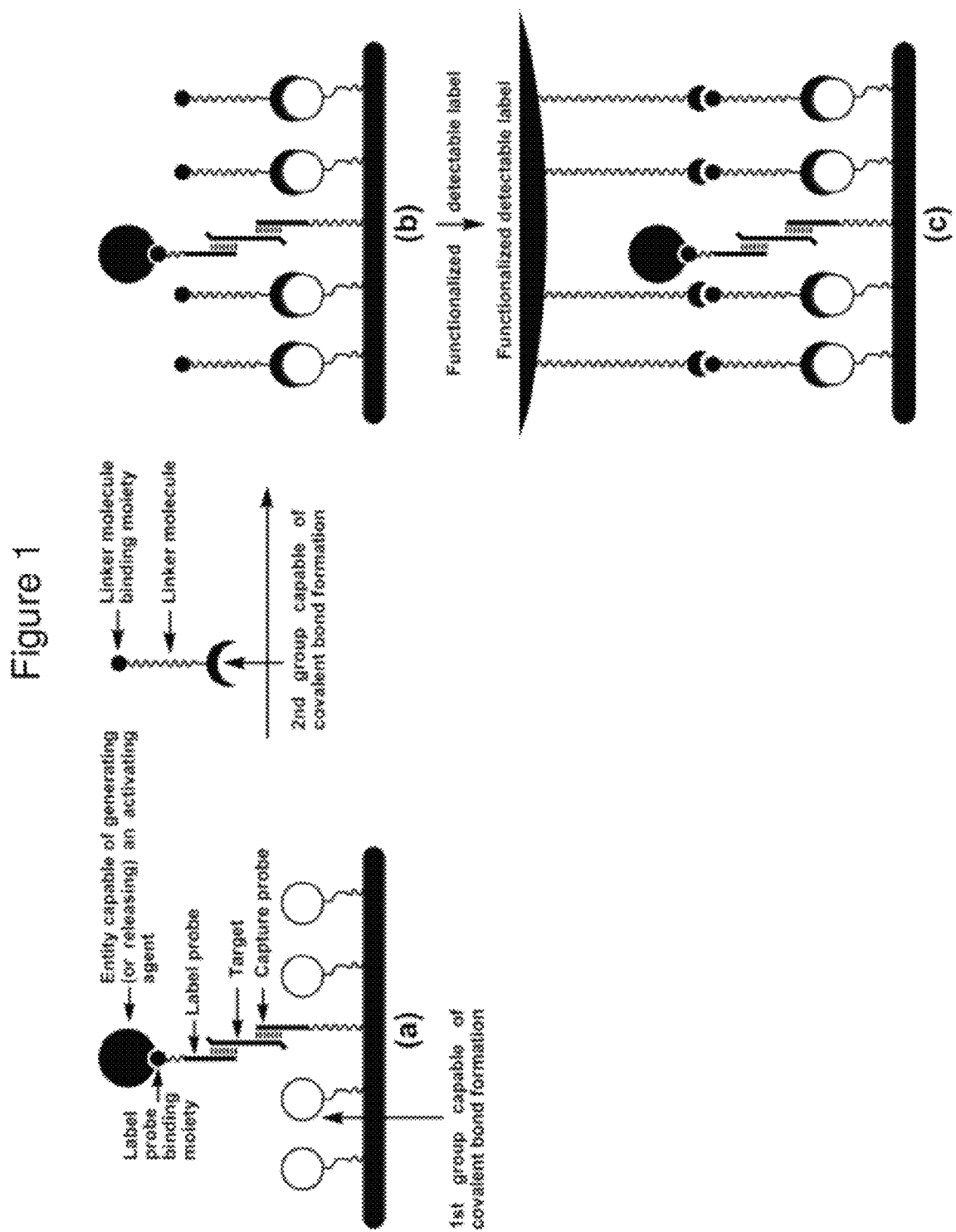
FIG. 1 illustrates binding complexes formed during a target detection method according to the present disclosure as follows: (a) A substrate functionalized with one or more target-specific capture probes and a plurality of molecules including $1^{st}$ covalent bond-forming reactive group(s) is provided. A reaction mixture including a target molecule, label probe, an entity capable of generating (or releasing) an activating agent, and the functionalized substrate results in formation of a substrate-immobilized complex including a substrate-bound target-specific capture probe, a target molecule, a label probe and an entity capable of generating (or releasing) an activating agent. (b) In the presence of an activating agent generated (or released), linker molecules including $2^{nd}$ covalent bond-forming reactive group(s) form covalent bonds with the substrate-bound $1^{st}$ covalent bond-forming reactive group(s) in a target-localized manner resulting in target-localized deposition of linker molecule binding moieties. (c) The addition of functionalized detectable label to the reaction mixture results in target-localized anchoring of the detectable label to the substrate surface via the linker molecule binding moieties of the linker molecules, which linker molecules are in turn covalently bonded to the substrate surface via the molecules including $1^{st}$ covalent bond-forming reactive group(s).

As used herein, the term "detectable label" refers to a molecule or particle able to be detected, including, but not limited to, fluorescent particles, chemiluminescent particles, magnetic particles (e.g., magnetic beads) and the like.

The term "linker molecule" is used herein to refer to a molecule including at least one covalent bond-forming reactive group as defined herein and at least one group that is either a member of a specific binding pair or a functional group capable of subsequent covalent bond formation.

The term "target-specific capture probe" is used herein to refer to a substrate-immobilized molecule that is capable of specifically binding to a target molecule or other analyte of interest when brought into contact with the target molecule or other analyte of interest under suitable reaction conditions.

The term "covalent bond forming reactive group" is used herein to refer to a $1^{st}$ group of a $1^{st}$ molecule capable of participating in specific covalent bond formation with a $2^{nd}$ group of a $2^{nd}$ molecule in the presence of a specific activating agent. In the absence of a specific activating agent, reaction between the $1^{st}$ and $2^{nd}$ groups to form a covalent bond does not proceed or proceeds at an insignificant rate. That is, the probability of covalent bond formation between the $1^{st}$ and $2^{nd}$ groups is significantly reduced. For example, under otherwise identical conditions, the probability of covalent bond formation between the $1^{st}$ and $2^{nd}$ groups in the absence of a specific activating agent may be less than 20%, e.g., less than 10%, less than 5%, or less than 1%.

The terms "target-specific label probe" and "label probe" are used herein to refer to a bi-functional molecule having a $1^{st}$ specific binding moiety capable of specifically binding at least a portion of a target molecule or other analyte of interest when brought into contact with the target molecule or other analyte of interest under suitable reaction conditions and a $2^{nd}$ specific binding moiety capable of specifically binding an entity capable of generating (or releasing) an activating agent when brought into contact with the entity capable of generating (or releasing) an activating agent under suitable reaction conditions.

As used herein, the term "entity capable of generating (or releasing) an activating agent" refers to a molecular entity, e.g., an enzyme conjugate, capable of specifically binding to a target molecule or other analyte of interest either directly or indirectly and initiating or catalyzing the formation of a covalent bond between a $1^{st}$ covalent bond-forming reactive group(s) and a $2^{nd}$ covalent bond-forming reactive group(s) and/or activating one or more of the $1^{st}$ and/or the $2^{nd}$ covalent bond forming reactive group(s) in the presence of an activating agent.

The terms "polypeptide" and "protein", used interchangeably herein, refer to a polymeric form of amino acids of any length, which can include natural and non-natural amino acids, chemically or biochemically modified or derivatized amino acids, and polypeptides having modified peptide backbones. The term includes fusion proteins, including, but not limited to, fusion proteins with a heterologous amino acid sequence, fusions with heterologous and native leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like.

The terms "nucleic acid," "nucleic acid molecule", "oligonucleotide" and "polynucleotide" are used interchangeably and refer to a polymeric form of nucleotides of any length, either deoxyribonucleotides or ribonucleotides, or compounds produced synthetically which can hybridize with naturally occurring nucleic acids in a sequence specific manner similar to that of two naturally occurring nucleic acids, i.e., can participate in Watson-Crick base pairing interactions. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, cDNA, recombinant polynucleotides, plasmids, vectors, isolated DNA of any sequence, control regions, isolated RNA of any sequence, nucleic acid probes, and primers.

The term "sequence" may refer to a particular sequence of bases and/or may also refer to a polynucleotide having a particular sequence of bases. Thus a sequence may be information or may refer to a molecular entity, as indicated by the context of the usage.

The term "moiety" is used to refer to a portion of an entity or molecule, typically having a particular function, structure, or structural feature.

The terms "antibody," "immunoglobulin" and their plural referents include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, and fusion proteins including an antigen-binding portion of an antibody and a non-antibody protein. The antibodies may be bound to an entity that enables their detection, e.g., a radioisotope, an enzyme which generates a detectable product, a fluorescent protein, and the like. The antibodies may be further covalently or non-covalently conjugated to other moieties, such as members of specific binding pairs, e.g., biotin (member of biotin-avidin/streptavidin specific binding pair), and the like. The antibodies may also be bound to a solid support, including, but not limited to, polystyrene plates or beads, and the like. Also encompassed by the terms are Fab', Fv, F(ab')2, and or other antibody fragments that retain specific binding to antigen.

Antibodies may exist in a variety of other forms including, for example, Fv, Fab, and (Fab')2, as well as bi-functional (i.e. bi-specific) hybrid antibodies (e.g., Lanzavecchia et al., *Eur. J. Immunol.* 17, 105 (1987)) and in single chains (e.g., Huston et al., *Proc. Natl. Acad. Sci. USA*, 85, 5879-5883 (1988); Bird et al., *Science*, 242, 423-426 (1988); see Hood et al., *Immunology*, Benjamin, N.Y., 2nd ed. (1984), and Hunkapiller and Hood, *Nature*, 323, 15-16 (1986)).

The terms "capable of hybridizing," "hybridizing" and "hybridization" as used herein refers to binding between complementary or partially complementary molecules, for example as between the sense and anti-sense strands of double-stranded DNA. Such binding is commonly non-covalent binding, and is specific enough such that binding may be used to differentiate between highly complementary molecules and others less complementary. Examples of highly complementary molecules include complementary oligonucleotides, DNA, RNA, and the like, which include a region of nucleotides arranged in the nucleotide sequence that is exactly complementary to a second nucleic acid sequence; examples of less complementary oligonucleotides include ones with nucleotide sequences including one or more nucleotides not in the sequence exactly complementary to a second oligonucleotide.

The term "complementary" references a property of specific binding between polynucleotides based on the sequences of the polynucleotides. As used herein, polynucleotides are complementary if they bind to each other in a hybridization assay under stringent conditions. Portions of polynucleotides are complementary to each other if they follow conventional base-pairing rules, e.g. A pairs with T (or U) and G pairs with C. "Complementary" includes embodiments in which there is an absolute sequence complementarity, and also embodiments in which there is a substantial sequence complementarity.

"Absolute sequence complementarity" means that there is 100% sequence complementarity between a first polynucleotide and a second polynucleotide, i.e. there are no insertions, deletions, or substitutions in either of the first and second polynucleotides with respect to the other polynucleotide (over the complementary region). Put another way, every base of the complementary region is paired with its complementary base following normal base-pairing rules.

"Substantial sequence complementarity" permits one or more relatively small (less than 10 bases, e.g. less than 5 bases, typically less than 3 bases, more typically a single base) insertions, deletions, or substitutions in the first and or second polynucleotide (over the complementary region) relative to the other polynucleotide. The complementary region is the region that is complementary between a first polynucleotide and a second polynucleotide (e.g. a distinct sequence of a nucleic acid target molecule and a target-specific capture probe). Complementary sequences are typically embedded within larger polynucleotides, thus two relatively long polynucleotides may be complementary over only a portion of their total length. The complementary region is typically at least about 10 bases long, more typically at least about 12 bases long, more typically at least about 15 bases long, still more typically at least about 20 bases long, or may be at least about 25 bases long.

The terms "hybridizing specifically to," "specific hybridization," "selectively hybridize to," and the like are used herein to refer to the binding, duplexing, or hybridizing of a nucleic acid molecule preferentially to a particular nucleotide sequence under "stringent conditions."

The term "stringent conditions" refers to conditions under which a first molecule, e.g., a first nucleic acid, will bind preferentially to a second molecule, e.g., a second nucleic acid, and to a lesser extent to, or not at all to, other sequences. Put another way, the term "stringent hybridization conditions" as used herein refers to conditions that are compatible to produce duplexes between complementary binding members, e.g., between a sequence of a target-specific capture probe and a complementary sequence of a target nucleic acid.

"Stringent hybridization conditions" and "stringent hybridization wash conditions" in the context of nucleic acid hybridization are sequence dependent, and are different under different environmental parameters. Stringent hybridization conditions can include, e.g., hybridization in a buffer including 50% formamide, 5× saline sodium citrate (SSC), and 1% sodium dodecyl sulfate (SDS) at 42° C., or hybridization in a buffer including 5×SSC and 1% SDS at 65° C., both with a wash of 0.2×SSC and 0.1% SDS at 65° C. Exemplary stringent hybridization conditions can also include a hybridization in a buffer of 40% formamide, 1 M NaCl, and 1% SDS at 37° C., and a wash in 1×SSC at 45° C. Yet additional stringent hybridization conditions include hybridization at 60° C. or higher and 3×SSC (450 mM NaCl/45 mM sodium citrate) or incubation at 42° C. in a solution containing 30% formamide, 1M NaCl, 0.5% sodium sarcosine, 50 mM 2-(N-morpholino)ethanesulfonic acid, pH 6.5. Those of ordinary skill will readily recognize that alternative but comparable hybridization and wash conditions can be utilized to provide conditions of similar stringency.

In certain embodiments, the stringency of the wash conditions may affect the degree to which nucleic acid molecules specifically hybridize. Suitable wash conditions may include, e.g.: a salt concentration of about 0.02 M at pH 7 and a temperature of at least about 50° C. or about 55° C. to about 60° C.; or, a salt concentration of about 0.15 M NaCl at 72° C. for about 15 min; or, a salt concentration of about 0.2×SSC at a temperature of at least about 50° C. or about 55° C. to about 60° C. for about 1 to about 20 min; or, multiple washes with a solution with a salt concentration of about 0.1×SSC containing 0.1% SDS at 20 to 50° C. for 1 to 15 min; or, equivalent conditions. Stringent conditions for washing can also be, e.g., 0.2×SSC/0.1% SDS at 42° C. In instances wherein the nucleic acid molecules are oligodeoxynucleotides (i.e. oligonucleotides made up of deoxyribonucleotide subunits), stringent conditions can include washing in 6×SSC/0.05% sodium pyrophosphate at 37° C. (for 14-base oligos), 48° C. (for 17-base oligos), 55° C. (for 20-base oligos), and 60° C. (for 23-base oligos). See Sambrook, et al., *Molecular Cloning: A Laboratory Manual*, Second Edition, (1989) Cold Spring Harbor, N.Y.), for detailed descriptions of equivalent hybridization and wash conditions and for reagents and buffers, e.g., SSC buffers and equivalent reagents and conditions.

Stringent hybridization conditions may also include a "prehybridization" of aqueous phase nucleic acids with complexity-reducing nucleic acids to suppress repetitive sequences. For example, certain stringent hybridization conditions include, prior to any hybridization to surface-bound polynucleotides, hybridization with Cot-1 DNA or with random sequence synthetic oligonucleotides (e.g. 25-mers), or the like.

Stringent hybridization conditions are hybridization conditions that are at least as stringent as the above representative conditions, where conditions are considered to be at least as stringent if they are at least about 80% as stringent, typically at least about 90% as stringent as the above specific stringent conditions. Other stringent hybridization conditions are known in the art and may also be employed, as appropriate.

The terms "bind" and "bound" as used herein refer to a binding interaction between two or more entities. Where two entities, e.g., molecules, are bound to each other, they may be directly bound, i.e., bound directly to one another, or they may be indirectly bound, i.e., bound through the use of an intermediate linking moiety or entity. In either case the binding may covalent; e.g., through covalent bonds; or non-covalent, e.g., through ionic bonds, hydrogen bonds, electrostatic interactions, hydrophobic interactions, Van der Waals forces, or a combination thereof.

The terms "specific binding," "specifically bind," and the like, refer to the ability of a first binding molecule or moiety (e.g., a target-specific binding moiety) to preferentially bind directly to a second binding molecule or moiety (e.g., a target molecule) relative to other molecules or moieties in a reaction mixture. In certain embodiments, the affinity between a first binding molecule or moiety and a second binding molecule or moiety when they are specifically bound to each other is characterized by a KD (dissociation constant) of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M, or less than $10^{-15}$ M.

As used herein a "member of a specific binding pair" is a member of a pair of molecules or entities that takes part in a specific binding interaction. Where a first member of the specific binding pair is identified, the identity of the second member of the specific binding pair is readily identifiable. It should be noted that when either member of the binding pair is referred to as the first member, the remaining member is understood to be the second member and vice versa. Examples of specific binding pair interactions include immune interactions such as antigen/antibody and hapten/antibody as well as non-immune interactions such as complementary nucleic acid binding, a sugar and a lectin specific therefore, an enzyme and an inhibitor therefore, an apoenzyme and cofactor, a hormone and a receptor therefore, biotin/avidin and biotin/streptavidin.

The term "alkyl" as used herein refers to a branched, unbranched or cyclic saturated hydrocarbon group of 1 to about 50 carbon atoms, such as methyl, ethyl, n-propyl, isopropyl, n-butyl, isobutyl, t-butyl, octyl, decyl, tetradecyl, hexadecyl, eicosyl, tetracosyl and the like. Preferred alkyl groups herein may contain 1 to about 36, more typically 1 to 10, carbon atoms. The term "lower alkyl" intends an alkyl group of 1 to 6 carbon atoms, preferably 1 to 4 carbon atoms. The alkyl groups present on the polymers described herein may be unsubstituted or they may be substituted with one or more substituents including functional groups (e.g., amine, hydroxyl, an olefinic group such as a vinyl or an allyl group), or the like. "Substituted alkyl" refers to alkyl substituted with one or more substituent groups, and this includes instances wherein two hydrogen atoms from the same carbon atom in an alkyl substituent are replaced, such as in a carbonyl group (i.e., a substituted alkyl group may include a —C(=O)— moiety). Other substituents include halogen, ether, hydroxyl, amine functional groups, etc. as defined in more detail below. The terms "heteroatom-containing alkyl" and "heteroalkyl" refer to an alkyl substituent in which at least one carbon atom is replaced with a heteroatom, such as O, S, P, or N, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "alkylene" as used herein refers to a difunctional saturated branched or unbranched hydrocarbon chain containing from 1 to 50 carbon atoms. "Lower alkylene" refers to alkylene linkages containing from 1 to 12 carbon atoms, and includes, for example, methylene (—CH$_2$—), ethylene (—CH$_2$CH$_2$—), propylene (—CH$_2$CH$_2$CH$_2$—), 2-methyl-propylene (—CH$_2$—CH(CH$_3$)—CH$_2$—), hexylene (—CH$_2$)$_6$—) and the like. As with alkyl groups, and unless otherwise specified, alkylene groups include linear, branched, cyclic, unsubstituted, substituted, and heteroatom-containing alkylene groups. Similarly, the terms "alkenylene," "alkynylene," "arylene," "alkarylene," and "aralkylene" refer to difunctional (i.e., linking) alkenyl, alkynyl, aryl, alkaryl, and aralkyl groups, respectively.

The term "alkenyl" as used herein refers to a linear, branched or cyclic hydrocarbon group of 2 to about 50 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein may contain 2 to about 36 carbon atoms, and for example may contain 2 to 12 carbon atoms. The term "lower alkenyl" intends an alkenyl group of 2 to 6 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively. Similarly, the term "olefin," as in an "olefinic compound" as used herein refers to a mono-unsaturated or di-unsaturated hydrocarbon of 2 to 36 carbon atoms, wherein in preferred embodiments a carbon-carbon double bond is positioned between the terminal 2 carbon atoms. Preferred olefinic groups within this class are sometimes herein designated as "lower olefinic groups," intending a hydrocarbon containing 2 to 18 carbon atoms containing a single terminal double bond. The latter moieties may also be termed "lower alkenyl." In some cases, it is a part of a silicon containing compound. Typically, but not necessarily, compounds containing olefinic groups are in a liquid form during use in the methods of the disclosure.

The term "alkynyl" as used herein refers to a linear or branched hydrocarbon group of 2 to 50 carbon atoms containing at least one triple bond, such as ethynyl, n-propynyl, and the like. Generally, although again not necessarily, alkynyl groups herein may contain 2 to about 18 carbon atoms, and such groups may further contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "aryl" as used herein refers to an aromatic species having 1 to 3 rings, but typically intends a mono-cyclic or bicyclic moiety, e.g., phenyl or 1- or 2-naphthyl groups. Optionally, these groups are substituted with 1 to 4, more preferably 1 to 2, substituents such as those described herein, including lower alkyl, lower alkoxy, hydroxyl, amino, and/or nitro. Aryl groups may, for example, contain 6 to 50 carbon atoms, and as a further example, aryl groups may contain 6 to 12 carbon atoms. For example, aryl groups may contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. If not otherwise indicated, the term "aryl" includes unsubstituted, substituted, and/or heteroatom-containing aromatic substituents.

The term "aralkyl" refers to an alkyl group with an aryl substituent, and the term "alkaryl" refers to an aryl group with an alkyl substituent, wherein "alkyl" and "aryl" are as defined above. In general, aralkyl and alkaryl groups herein contain 6 to 50 carbon atoms. Aralkyl and alkaryl groups may, for example, contain 6 to 20 carbon atoms, and as a further example, such groups may contain 6 to 12 carbon atoms.

The terms "alkoxy" and "aryloxy" refer to an alkyl group and aryl group, respectively, bound through an oxygen linkage. In some embodiments, the alkyl or aryl group binds through the oxygen linkage to a non-carbon element, such as to a silicon atom. "Lower alkoxy" intends an alkoxy group containing 1 to 10, more preferably 1 to 7, carbon atoms. The terms "oxyalkylene" and "oxyarylene" refer to bifunctional (i.e., linking) alkoxy and aryloxy groups, respectively.

The term "amino" intends an amino group —$NR_2$ where R is hydrogen or an alternative substituent, typically lower alkyl. The term "amino" is thus intended to include primary amino (i.e., $NH_2$), "alkylamino" (i.e., a secondary amino group containing a single alkyl substituent), and "dialkylamino" (i.e., tertiary amino group containing two alkyl substituents).

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, furyl, pyrimidinyl, imidazolyl, 1,2,4-triazolyl, tetrazolyl, etc., and examples of heteroatom-containing alicyclic groups are pyrrolidino, morpholino, piperazino, piperidino, tetrahydrofuranyl, etc.

"Hydrocarbyl" refers to univalent hydrocarbyl radicals containing 1 to about 50 carbon atoms, including 1 to about 36 carbon atoms, further including 1 to about 18 carbon atoms, and further including about 1 to 12 carbon atoms, including linear, branched, cyclic, saturated and unsaturated species, such as alkyl groups, alkenyl groups, aryl groups, and the like. "Substituted hydrocarbyl" refers to hydrocarbyl substituted with one or more substituent groups, and the term "heteroatom-containing hydrocarbyl" refers to hydrocarbyl in which at least one carbon atom is replaced with a heteroatom such as O, N, P, Si, or S. Examples of substituted hydrocarbyl groups include alkaryl, aralkyl, and the like; examples of heteroatom-containing hydrocarbyl groups include alkoxy, alkylamino, and the like. Unless otherwise indicated, the term "hydrocarbyl" is to be interpreted as including substituted and/or heteroatom-containing hydrocarbyl moieties. Furthermore, the term "hydrocarbylene" refers to a bivalent (i.e., linking) hydrocarbyl group, and unless otherwise indicated, includes substituted and/or heteroatom-containing hydrocarbylene moieties.

The term "ether" includes both mono and polyethers and refers to groups having a chain containing carbon and oxygen and each of these units consists of 2 to 6 carbons for each oxygen atom. Examples are diethyl and dipropyl ethers, polyethyleneoxide, polyprolyleneoxide, polyethelene glycol, polybuteleneoxide.

"Halo" or "halogen" refers to fluoro, chloro, bromo or iodo, and usually relates to halo substitution for a hydrogen atom in an organic compound.

As used herein, the term "perfluoro," such as a perfluoro group, perfluoro monomer, perfluoro oligomer or perfluoro polymer, refers to a moiety or compound in which fluoro atoms substitute for hydrogen atom completely or almost completely. In some embodiments of perfluoro groups, the hydrogen atoms on between 1 and 3 carbons at a terminus or at a terminal bonding site (i.e., where the group attaches to a substrate or to another chemical moiety) are not replaced with fluoro atoms. Perfluoro groups further include polycarbon or polyether chains having the hydrogen atoms replaced with fluoro atoms.

The terms "halocarbyl" and "halocarbon" refer to hydrocarbyl groups (as defined above) for which one or more hydrogen radicals are replaced with halo radicals. Similarly, the term "perhalocarbyl" refers to hydrocarbyl groups for which all hydrogen radicals are replaced with halo radicals. The terms "halocarbyl" and "halocarbon" include perhalocarbyl, and further includes fluorocarbyl groups, perfluorinated hydrocarbyl groups, chlorocarbyl groups, perchlorinated hydrocarbyl groups, bromocarbyl groups, perbrominated hydrocarbyl groups, iodocarbyl groups, and periodinated hydrocarbyl groups. Similarly, the term "haloether" refers to an ether group in which one or more hydrogen radicals are replaced with halo radicals, and the term "perhaloether" refers to an ether in which all hydrogen radicals are replaced with halo radicals. The term "haloether" includes perhaloethers, unless otherwise specified.

The terms "polymeric moiety" and "polymeric group" refer to a group containing two more repeating subunits linked in a linear, branched, hyperbranched, dendritic, or cyclic sequence, or any combination thereof. The subunits themselves may further be linear, branched, or cyclic. Furthermore, the subunits may contain heteroatoms such that the polymeric moiety has a backbone including heteroatoms. The terms also include copolymeric moieties, which are polymeric moieties consisting of two or more subunits. Unless otherwise specified, copolymers include architectures such as random, block, comb, and star, as well as combinations thereof. Polymeric moieties include synthetic as well as naturally occurring moieties, or fragments thereof. Examples of subunits include alkylene, arylene, heteroalkylene, amino acids, nucleic acids, saccharides, and the like. Similarly, the term "polymeric linker" refers to a bifunctional (i.e., linking) polymeric moiety. Examples of polymeric moieties include poly(ethylene glycol), poly(ethyleneamine), and poly(amino acid) groups.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation, functional groups and the hydrocarbyl moieties $C_1$-$C_{24}$ alkyl (including $C_1$-$C_{18}$ alkyl, further including $C_1$-$C_{12}$ alkyl, and further including $C_1$-$C_6$ alkyl), $C_2$-$C_{24}$ alkenyl (including $C_2$-$C_{18}$ alkenyl, further including $C_2$-$C_{12}$ alkenyl, and further including $C_2$-$C_6$ alkenyl), $C_2$-$C_{24}$ alkynyl (including $C_2$-$C_{18}$ alkynyl, further including $C_2$-$C_{12}$ alkynyl, and further including $C_2$-$C_6$ alkynyl), $C_5$-$C_{30}$ aryl (including $C_5$-$C_{20}$ aryl, and further including $C_5$-$C_{12}$ aryl), and $C_6$-$C_{30}$ aralkyl (including $C_6$-$C_{20}$ aralkyl, and further including $C_6$-$C_{12}$ aralkyl). By a "functional group" is meant a group that contains one or more reactive moieites. Examples of functional groups include halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO—), carbamoyl (—(CO)—NH$_2$), mono-substituted $C_1$-$C_{24}$ alkylcarbamoyl (—(CO)—NH($C_1$-$C_{24}$ alkyl)), di-substituted alkylcarbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano (—C≡N), isocyano (—N+≡C—), cyanato (—O—C≡N), isocyanato (—O—N≡C—), isothiocyanato (—S—C≡N), azido (—N=N+=N—), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_5$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{20}$ alkaryl, $C_6$-$C_{20}$ aralkyl, etc.), alkylimino (—CR=N(alkyl), where R=hydrogen, alkyl, aryl, alkaryl, etc.), arylimino (—CR=N (aryl), where R=hydrogen, alkyl, aryl, alkaryl, etc.), nitro (—NO$_2$), nitroso (—NO), sulfo (—SO$_2$—OH), sulfonato (—SO$_2$—O—), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O—)$_2$), phosphinato (—P(O)(O—)), phospho (—PO$_2$), and phosphino (—PH$_2$), mono- and di-($C_1$-$C_{24}$ alkyl)-substituted phosphino, and mono- and di-($C_5$-$C_{20}$ aryl)-substituted phosphino. In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl and aryl" is to be interpreted as "substituted alkyl and substituted aryl."

Unless otherwise specified, reference to an atom is meant to include isotopes of that atom. For example, reference to H is meant to include 1H, 2H (i.e., D) and 3H (i.e., T), and reference to C is meant to include $^{12}$C and all isotopes of carbon (such as $^{13}$C).

It will be appreciated by those of skill in the art that many of the above-provided definitions overlap in scope and are not meant to be mutually exclusive. Accordingly, any particular chemical group may fall within more than one of the above-provided definitions.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "a linker molecule" includes a plurality of such linker molecules and reference to "the binding complex" includes reference to one or more binding complexes and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The following Detailed Description and Examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius (° C.), and pressure is at or near atmospheric. Standard abbreviations may be used, e.g., bp, base pair(s); kb, kilobase(s); microliter(s); pl, picoliter(s); μm, micrometer/micron; s or sec, second(s); min, minute(s); h or hr, hour(s); aa, amino acid(s); kb, kilobase(s); bp, base pair(s); nt, nucleotide(s); and the like.

DETAILED DESCRIPTION

The present disclosure is directed to methods and compositions for use in connection with the qualitative and/or quantitative detection of target molecules and other analytes of interest that are spatially dispersed on a substrate surface. In one aspect, highly reactive, functionalized substrates are provided which may be used in connection with methods involving the target-localized deposition of detectable label. Also provided are various molecules including covalent bond-forming reactive groups. These molecules may be used to functionalize substrate surfaces and/or detectable labels for use in target detection. The present disclosure also provides linker molecules which may be used with a functionalized substrate surface or detectable label in methods involving the target-localized anchoring of detectable label. Finally, the present disclosure provides kits and methods for use in connection with methods involving the target-localized deposition of detectable label.

Functionalized Substrates

In one aspect, the present disclosure provides substrates having surfaces functionalized with molecules including one or more covalent bond-forming reactive groups. Suitable substrates for functionalization may be prepared from a variety of materials including, but not limited to, glass slides, fused silica, silicon and plastic.

In particular embodiments disclosed herein, substrates of interest include silicon-based materials embedded with magnetic sensors capable of detecting the presence of a magnetic particle immobilized on the surface of the substrate. For descriptions of such sensors, see, e.g., Baselt et al., *Biosens. Bioelectron.*, 13, 731-739 (1998); Edelstein et al., *Biosens. Bioelectron.*, 14, 805-813 (2000); Miller et al., *J. Magn. Magn. Mater.*, 225, 138-144 (2001); Graham et al. *J. Appl. Phys.*, 91, 7786-7788 (2002); Ferreira et al. *J. Appl. Phys.*, 93, 7281 (2003); Li et al. *J. Appl. Phys.*, 93, 7557-7559 (2003), May; Li et al. *IEEE Trans. Magn.*, 40, 3000 (2004); Wang et al., *J. Magn. Magn. Mater.*, 293, 731-736 (2005); Shen et al. *Appl. Phys. Lett.*, 86, 253901 (2005); Baselt et al. U.S. Pat. No. 5,981,297; Tondra, U.S. Pat. No. 6,743,639; and Tondra U.S. Pat. No. 6,875,621.

Substrates for use in connection with the present disclosure may have a variety of shapes and sizes. For example, in some embodiments a suitable substrate has a solid, substantially planar structure. In other embodiments, a suitable substrate may have a substantially spherical structure, e.g., a bead.

The substrate materials provide a support structure for the attachment of molecules including a covalent bond-forming reactive group(s). Such molecules provide a functionalized surface by providing locations for the deposition of linker molecules or the anchoring of detectable labels which include covalent bond-forming reactive group(s), e.g., as depicted generally in FIGS. 1 and 2.

A variety of single-step or multi-step methods may be used to attach molecules including covalent bond-forming reactive groups to the substrate surface. For example, in one embodiment, a silicon wafer substrate derivatized with aminoalkyl silane may be utilized in combination with carbodiimide activation of carboxylic acid groups present in the molecules including a covalent bond-forming reactive group(s), resulting in conjugation of the molecules including a covalent bond-forming reactive group(s) to the substrate surface. In another embodiment, the amino groups of the aminoalkyl silane derivatized on the substrate surface may be converted to maleimide groups using bifunctional molecules including NHS ester and maleimide groups separated by a polyethylene glycol (PEG) spacer. Molecules including a covalent bond forming reactive group(s) and a sulfhydryl group may then be conjugated to the substrate by reacting with the maleimide groups on the substrate surface.

Molecules including a covalent bond-forming reactive group(s), which are suitable for conjugation to the substrate surface to provide a functionalized substrate surface, may have a variety of structures. These molecules may be bi- or multi-functional reagents having any of a variety of suitable structures. For example, molecules suitable for functionalization of a substrate surface may be linear, branched or dendritic and may include one or more spacers linking the functional moieties of the molecules. Suitable spacers may have a variety of structures provided they are capable of effectively positioning the various functional moieties of the molecules, e.g., the covalent bond-forming reactive group(s), relative to the substrate surface. Suitable spacers may include, for example, polymers (e.g., PEG based polymers); alkyl groups, etc. The length of the spacer portion (or other suitable portion of the molecules) may be adjusted taking into account the length and/or size of one or more of the capture probe, the target molecule or analyte of interest, the label probe, and the entity capable of generating (or releasing) an activating agent, such that one or more covalent bond-forming reactive groups are positioned at a distance from the surface of the substrate and proximal to a complex including the entity capable of generating (or releasing) an activating agent, the label probe, the target molecule or analyte of interest, and the capture probe, wherein the complex is immobilized on the substrate surface. This may increase the likelihood of a covalent bond-forming reaction occurring between molecules functionalizing the substrate surface and either the linking molecules or a suitably functionalized detectable label.

The relative position of the covalent bond-forming reactive groups in the molecules may vary provided they are effectively positioned relative to the substrate surface and the target binding complex, when present, to provide for the target localized deposition of detectable label when present. For example, in some embodiments, a molecule including a covalent bond forming reactive group(s) includes a covalent bond forming reactive group in a terminal position relative to the molecule's attachment point to the substrate surface. Such embodiments may also include one or more covalent bond-forming reactive groups positioned between a terminal end of the molecule and the molecule's attachment point to the substrate surface.

In other embodiments the molecules including a covalent bond-forming reactive group(s) do not include a terminally positioned covalent bond-forming reactive group but instead include one or more covalent bond-forming reactive groups positioned between a terminal end of the molecule and the molecule's attachment point to the substrate surface.

In some embodiments, the molecules including covalent bond-forming reactive group(s) do not have the structure of a naturally occurring molecule, e.g., a naturally occurring nucleic acid or protein molecule. In some embodiments, the covalent bond-forming reactive group(s) themselves do not have the structure of a covalent bond forming reactive group(s) of a naturally occurring nucleic acid or protein molecule. For example, in some embodiments, the covalent bond-forming reactive group(s) are reactive groups other than tyrosine and thymine.

In some embodiments, the molecules including a covalent bond-forming reactive group(s) include a polymeric structure, e.g., a polymeric spacer structure. In some such embodiments, the covalent bond-forming reactive group(s) includes an aromatic ring structure(s). In some embodiments, a suitable substrate-functionalization molecule including a covalent bond-forming reactive group(s) includes a moiety capable of bonding to a substrate surface, a polymeric spacer structure, and one or more covalent bond-forming reactive groups. In some embodiments, the moiety capable of bonding directly or indirectly to a substrate surface is a specific binding moiety, e.g., a member of a specific binding pair as defined herein. In other embodiments the moiety capable of bonding directly or indirectly to a substrate surface includes a covalent bond-forming reactive group.

Suitable covalent bond-forming reactive groups may include aromatic groups, e.g., phenolic groups. In some embodiments, the aromatic group is tyramine or a tyramine derivative. In other embodiments, the aromatic group is thymine or a thymine derivative. Where the covalent bond-forming reactive group or groups are aromatic groups, the aromatic groups may, in some embodiments, include a plurality of electron-donating substituents on the aromatic ring, including alkyl and oxyalkyl groups and unsaturated systems.

The covalent bond-forming reactive groups may be selected based on the particular entity capable of generating (or releasing) an activating agent which is to be utilized therewith and vice versa. For example, phenolic groups may be selected where the entity capable of generating (or releasing) an activating agent is a peroxidase conjugate, e.g., HRP conjugate, or other entity capable of generating a free radical which results in covalent bond formation between a phenolic group and another covalent bond forming reactive group. However, other combinations of entities capable of generating (or releasing) an activating agent and covalent bond-forming reactive groups are known in the art and such may be utilized in connection with the disclosed methods and compositions. For example, one or more glycosidic bonds may be utilized as covalent bond-forming reactive groups in connection with a glycosidase conjugate capable of cleaving the glycosidic bond to expose an aldehyde group which can in turn form a covalent bond with an amino or hydrazide covalent bond forming reactive group.

The molecules including covalent bond-forming reactive group(s) may include a single participating reactive group or a plurality of participating reactive groups. Where the molecules including a covalent bond-forming reactive group(s) include a plurality of covalent bond-forming reactive groups, the number of covalent bond-forming reactive groups in the molecule may be 2, 3, 4, 5, 6, 7, 8, 9, 10 or more.

In some embodiments, the molecules including covalent bond-forming reactive groups are copolymers containing polymer units with a high concentration of covalent bond-forming reactive groups. For example, in some embodiments, a copolymer is utilized in which the ratio of polymer units containing covalent bond-forming reactive groups to polymer units which do not contain covalent bond-forming reactive groups is at least 1:20, at least 1:10, at least 1:4, at least 1:3, at least 1:2, at least 1:1, at least 2:1, at least 3:1, at least 4:1, at least 5:1, at least 6:1, at least 7:1, at least 8:1, at least 9:1, or at least 10:1.

In some embodiments, a substrate according to the present disclosure is functionalized with a plurality of polymers including phenolic and carboxylic acid subunits, e.g., a tyrosine-glutamate copolymer or a tyrosine-aspartate copolymer.

In some embodiments, a substrate surface is functionalized with a plurality of molecules, e.g., polymers, including a plurality of $1^{st}$ covalent bond-forming reactive groups (e.g., phenolic groups) capable of forming covalent bonds with linker molecules (or suitably functionalized detectable label) as described herein. In addition, the molecules may include a plurality of $2^{nd}$ groups capable of conjugating with capture probes as described herein. These $2^{nd}$ groups can be members of one of the specific pairs of functional groups commonly used in chemical conjugations while the capture probes include the other member of the pair for forming the chemical conjugations. Such specific pairs of functional groups for forming chemical conjugations are known in the art. Some examples for such pairs are amino groups pairing with NHS esters, sulfhydryl groups pairing with maleimide groups, hydrazine derivatives paring with aldehyde groups, etc. In this manner, a substrate surface may be functionalized with both covalent bond-forming reactive groups, which are available to form covalent bonds with linker molecules (or suitably functionalized detectable label), and capture probes by conjugating the capture probes to the molecules including the covalent-bond forming reactive groups, e.g., as opposed to conjugating the capture probes directly to the substrate surface via a suitable conjugation chemistry.

Molecules including covalent bond-forming reactive groups, which are suitable for conjugation to the substrate surface to provide a functionalized substrate surface, may have a structure as set forth in formula (I) below:

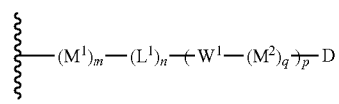

(I)

wherein:
the wavy line represents the attachment point to the surface;
m and n are integers independently selected from 0 and 1;
p is an integer equal to 0 or greater, provided that when n is 0, then p is not 0;
q is an integer selected from 0 and 1;
$L^1$ is selected from unsubstituted alkylene, substituted alkylene, heteroatom-containing alkylene, substituted heteroatom-containing alkylene, unsubstituted alkenylene, substituted alkenylene, heteroatom-containing alkenylene, substituted heteroatom-containing alkenylene, unsubstituted arylene, substituted arylene, heteroarylene, substituted heteroarylene, and polymeric linkers;
$M^1$ and each instance of $M^2$ are independently selected from a bond, unsubstituted alkylene, substituted alkylene, heteroatom-containing alkylene, substituted heteroatom-containing alkylene, unsubstituted alkenylene, substituted alkenylene, heteroatom-containing alkenylene, substituted heteroatom-containing alkenylene, unsubstituted arylene, substituted arylene, heteroarylene, and substituted heteroarylene;
each instance of $W^1$ is selected from the group consisting of alkylene, arylene, heteroatom-containing alkylene, and heteroarylene, provided that $W^1$ is substituted with a group including a moiety selected from alkene, aryl, azide, and α,β-unsaturated carbonyl; and
D is an endgroup that is selected from H, unsubstituted alkyl, substituted alkyl, heteroatom-containing alkyl, substituted heteroatom-containing alkyl, unsubstituted alkenyl, substituted alkenyl, heteroatom-containing alkenyl, substituted heteroatom-containing alkenyl, unsubstituted aryl, substituted aryl, heteroaryl, and substituted heteroaryl, wherein D is optionally substituted with a group including a moiety selected from alkene, aryl, azide, and α,β-unsaturated carbonyl.

For example, in some embodiments of formula (I), $W^1$ has the structure

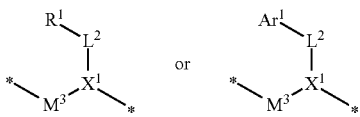

wherein:

$X^1$ is —CH— or —N—;

$M^3$ is a linker moiety selected from alkylene, substituted alkylene, heteroatom-containing alkylene, and substituted heteroatom-containing alkylene;

$L^2$ is a linker that may be a bond (i.e., a direct linkage) or may be selected from alkylene, alkenylene, and arylene, any of which may be substituted or unsubstituted and may contain one or more heteroatoms;

$Ar^1$ is an aromatic moiety including at least one electron donating substituent, and which may be further substituted with one or more substituents, may include one or more heteroatoms, and may include two or more fused aromatic rings; and $R^1$ is an unsaturated moiety selected from alkylene, substituted alkylene, alkenylene, substituted alkenylene,

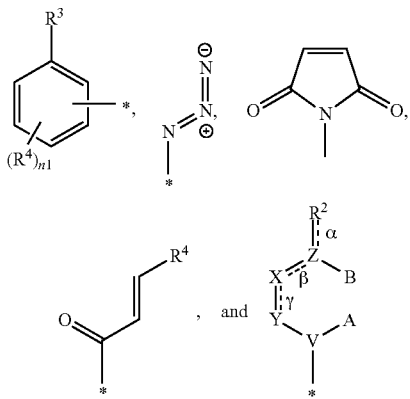

wherein:

$R^3$ is selected from OH and $NH_2$;

n1 is selected from 0, 1, 2, 3, and 4;

each $R^4$ is independently selected from H, hydrocarbyl, substituted hydrocarbyl, heteroatom-containing hydrocarbyl, substituted heteroatom-containing hydrocarbyl, and functional groups;

α, β, and γ are optional bonds, provided that either β is present or α and γ are present;

A and B are independently selected from H, substituted or unsubstituted alkyl, substituted or unsubstituted alkene, and functional groups, or A and B are selected from carbon and nitrogen and are taken together to form a cycle;

Y is $CR^a$ or N if γ is present and C(=O), $C(R^a)_2$, $NR^a$, S, and O if γ is absent;

X is $CR^a$ or N;

Z is $CR^a$ or N, provided that B is absent if Z is N;

$R^2$ is O, $C(R^a)_2$, or $NR^a$ if α is present and $C(R^a)_3$, $N(R^a)_2$, $SR^a$, or $OR^a$ if α is absent;

V is selected from $CR^a$, N, S, and O, provided that A is absent if V is S or O; and $R^a$ is selected from H, hydrocarbyl, substituted hydrocarbyl, heteroatom-containing hydrocarbyl, and substituted heteroatom-containing hydrocarbyl.

For example, in some embodiments, $W^1$ is an amino acid such as tyrosine (i.e., a heteroalkylene substituted with an aralkyl group and having a carbonyl group). In some embodiments, $M_2$ is a bond or an alkylene linker.

For example, in some embodiments of formula (I), D is an amino acid such as tyrosine. Also for example, D has the structure

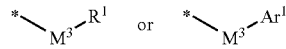

wherein $M^3$, $R^1$, and $Ar^1$ are as defined above.

For example, in some embodiments of formula (I), $L^1$ is a polymeric linker moiety. Examples of such include poly(ethyleneimine) and poly(alkyleneoxide) linker moieties, such as poly(methylene oxide) (i.e., $(-OCH_2-)_n$), polyethylene oxide) (i.e., $(-OCH_2CH_2-)_n$), poly(propylene oxide) (i.e., $(-OCH_2CH(CH_3)-)_n$), or the like. Other examples of polymeric linking moieties include poly(amino acid)s, poly(saccharide)s, and poly(nucleic acid)s. Where $L^1$ is a polymeric linking moiety, the molecular weight of $L^1$ may be between about 100 Da and about 100,000 Da, or between about 100 Da and 10,000 Da, or between about 100 D and 1,000 Da. In some embodiments, $L^1$ has block-like character. For example, $L^1$ may include two, three, four, or more blocks of any size of the above-mentioned example polymeric moieties. In other embodiments, $L^1$ is not a polymeric moiety in the sense that it does not have an identifiable repeating moiety. Examples of such $L^1$ groups include an amino acid (e.g., tyrosine).

For example, in some embodiments of formula (I), $M^1$ and $M^2$ are linking moieties containing a moiety selected from alkyl groups, amide groups, ether groups, ester groups, and combinations thereof. Examples include $-(CH_2)$, $-C(=O)-NH-$, $-(OCH_2CH_2)$, $-C(=O)-NH-$, $-C(=O)-NH-CH_2CH_2-(OCH_2CH_2)_n-C(=O)-NH-$, $-C(=O)-NH-(CH_2)_n-C(=O)-NH-$, and the like, wherein n is an integer equal to or greater than 0.

Also for example, in some embodiments, $Ar^1$ has the structure

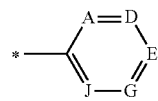

wherein

A, D, E, G, and J are selected from C—R and N, wherein each R is independently selected from H, alkyl, alkenyl, aryl, oxygen-containing substituents, and nitrogen-containing substituents, provided that any two adjacent R groups may be taken together to form a cycle that is optionally further substituted and optionally further heteroatom-containing. In some embodiments, no more than one, or no more than 2, or no more than 3, or no more than 4 of A, D, E, G, and J is N.

Also for example, in some embodiments, $Ar^1$ has the structure

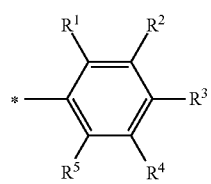

wherein each of $R^1$-$R^5$ are independently selected from H, alkyl, alkenyl, aryl, hydroxyl, amino, alkoxy, mono-alkyl-substituted amino, di-alkyl-substituted amino, and amido.

In some embodiments, $R^3$ is selected from H, alkyl, alkenyl, amino, alkoxy, alkyl-substituted amino, amido, and aryl; and at least one of $R^1$, $R^2$, $R^4$, and $R^5$ is hydroxyl, amino, alkoxy, alkyl-substituted amino, or amido. In some such embodiments, at least one of $R^1$, $R^2$, $R^4$, and $R^5$ is hydroxyl.

In addition to the molecules including covalent bond-forming reactive groups, functionalized substrates according to the present disclosure may also include one or more target-specific capture probes bound thereto. See, e.g., FIG. 1 which illustrates a substrate functionalized with a plurality of molecules including a covalent bond-forming reactive group, and a target-specific capture probe. These target-specific capture probes may have a variety of structures provided that they are capable of specifically binding to a target molecule or other analyte of interest under suitable reaction conditions. For example, where the target molecule is a nucleic acid, a suitable target-specific capture probe may be a nucleic acid molecule having a region of sequence complementarity to a region of the target nucleic acid molecule, e.g., a region of substantial or absolute sequence complementarity. Where the target molecule is a protein or fragment thereof a suitable target-specific capture probe may be an antibody capable of specifically binding to the target molecule. Additional binding members capable of specific interactions are known in the art and accordingly a suitable target-specific capture probe may be readily identified and prepared for a specific target molecule or analyte of interest using standard techniques.

Where a functionalized substrate according to the present disclosure includes both target-specific capture probes and molecules including a covalent bond-forming reactive group(s), these two types of molecules may be distributed on the substrate surface such that they are positioned in proximity to each other. In some embodiments, the ratio of molecules including a covalent bond-forming reactive group(s) to target-specific capture probes, per unit area, is at least 1:20, at least 1:10, at least 1:5, at least 1:1, at least 2:1, at least 3:1, at least 4:1, at least 5:1, at least 6:1, at least 7:1, at least 8:1, at least 9:1, or at least 10 to 1.

Detectable Labels

There are a variety of detectable labels known in the art which can be utilized in connection with the disclosed methods and compositions. These include, for example, fluorescent particles, chemiluminescent particles and magnetic particles.

In one embodiment of the methods and compositions disclosed herein, a detectable label is utilized, wherein the detectable label is a magnetic particle, e.g., a magnetic nano-particle or micro-particle. Magnetic particles include, for example, magnetic beads or other small objects made from a magnetic material such as a ferromagnetic material, a ferrimagnetic material, a paramagnetic material, or a superparamagnetic material. In some embodiments, the magnetic particles include iron oxide ($Fe_2O_3$ and/or $Fe_3O_4$) with diameters ranging from about 10 nm to about 100 μm. Magnetic nanoparticles are available, for example, from Miltenyi Biotec Corporation of Bergisch Gladbach, Germany. These are relatively small particles made from coated single-domain iron oxide particles, typically in the range of about 10 to about 100 nm in diameter. Magnetic particles can also be made from magnetic nanoparticles embedded in a polymer matrix such as polystyrene. Such particles may have diameters of about 1 to about 5 μm. Particles of this type are available from Invitrogen Corporation, Carlsbad, Calif. Additional examples of magnetic particles include those described by Baselt et al., *Biosens. Bioelectron.*, 13, 731-739 (1998); Edelstein et al., *Biosens. Bioelectron.*, 14, 805-813 (2000); Miller et al., *J. of Mag. Magn. Mater.*, 225, 138-144 (2001); Graham et al., *J. Appl. Phys.*, 91, 7786-7788 (2002); Ferreira et al. *J. Appl. Phys.*, 93, 7281-7286 (2003); and U.S. Patent Application Publication No. 2005/0100930 (published May 12, 2005).

In some embodiments, a detectable label, e.g., a magnetic or non-magnetic particle, for use in connection with the present disclosure may have a diameter of from about 100 nm to about 5 μm e.g., from about 200 nm to about 4 from about 300 nm to about 3 μm, from about 400 nm to about 2 μm, or from about 500 nm to about 1 μm.

A suitable detectable label may be one which is detectable using a microscopy system which may or may not utilize specifically detectable characteristics of the detectable label such as fluorescence or magnetic field. For example, in some embodiments, a suitable detectable label may be detectable by an optical microscopy system based solely on its size. This may be the case, for example, where a detectable particle is used which has a diameter of 0.1 μm or more, e.g., 0.5 μm or more.

Detectable label particles for use in connection with the disclosed methods and compositions include surfaces functionalized with molecules bound thereto. In some embodiments, the detectable label particles are functionalized with molecules including covalent bond-forming reactive groups as described herein. See, e.g., FIGS. 2, 4, 8 and 9. In other embodiments, the detectable label particles are functionalized with molecules which are capable of specifically binding linker molecule binding moieties. See, e.g., FIG. 1(c). The functionalized detectable label binding moieties and linker molecule binding moieties described herein may include members of a specific binding pair as defined previously herein.

In some embodiments, a detectable label particle suitable for use in connection with the disclosed methods and compositions includes a surface functionalized with molecules including covalent bond-forming reactive groups, wherein the molecules have structures which are similar or the same as those discussed above in the context of the functionalized substrate surfaces, e.g., as set forth in formula (I). In such embodiments, the wavy line of formula (I) represents a covalent attachment to a detectable label particle.

In other embodiments, a detectable label particle suitable for use in connection with the disclosed methods and compositions includes a surface functionalized with molecules having the structure of formula (II):

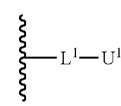

(II)

wherein $L^1$ is as defined above for formula (I);

$U^1$ is a member of a specific binding pair (e.g., a first or second member of a specific binding pair) or a covalent bond-forming reactive group; and the wavy line represents a covalent attachment to the detectable label particle.

In some embodiments, $U^1$ is selected from a biotin moiety, a nucleic acid sequence, an antigen, an antibody, a hapten or an antigen, an avidin or streptavidin moiety, a sugar moiety, and a lectin moiety.

In some embodiments, a detectable label particle suitable for use in connection with the disclosed methods and compositions includes a surface functionalized with molecules having the structure of formula (III):

(III)

wherein
$L^1$ and
D are as defined above for formula (I), and
the wavy line represents a covalent attachment to the detectable label particle.

Linker Molecules

The present disclosure provides linker molecules for use in connection with the compositions, methods and kits described herein. These linker molecules, as depicted for example in FIG. 1, include at least one specific binding moiety or a functional group capable of subsequent covalent bond formation, referred to herein as a "linker molecule binding moiety", e.g., a member of a specific binding pair as defined herein, and at least one covalent bond-forming reactive group as defined herein. The linker molecules according to the present disclosure are configured for use with a functionalized substrate and one or more detectable labels as described herein. Accordingly, the linker molecule binding moiety of the linker molecule is configured to specifically bind or form one or more covalent bonds with a suitable functionalized detectable label as described herein, and the covalent bond-forming reactive group is configured to form a covalent bond with a covalent bond-forming reactive group of a molecule attached to the substrate surface as described herein. See, e.g., FIG. 1(c), which illustrates a binding complex wherein the binding moiety of the linker molecule is bound to a detectable label functionalized with a binding moiety of the detectable label. In addition, a covalent bond-forming reactive group(s) of the linker molecule forms a covalent bond(s) with a covalent bond-forming reactive group(s) of a molecule immobilized on the substrate surface. As shown, such a binding complex can result in immobilization of a detectable label on the substrate surface via multiple anchoring linkages.

Similarly to the molecules used to functionalize either a substrate surface or a detectable label as described previously herein, linker molecules may have a variety of structures. The linker molecules may be bi- or multi-functional reagents having any of a variety of suitable structures. For example, linker molecules may be linear or dendritic and may include one or more spacers linking the functional moieties of the molecules. Suitable spacers may have a variety of structures provided they are capable of effectively positioning the various functional moieties of the molecules, e.g., the covalent bond-forming reactive group(s) relative to the linker molecule binding moiety. Suitable spacers may include, for example, polymers (e.g., PEG based polymers); alkyl groups, etc. The length of the spacer portion (or other suitable portion of the linker molecules) may be adjusted, e.g., taking into account the size of the detectable, label to be used and/or the length and/or size of the target binding complex to be formed (e.g., the length and/or size of the capture probe, the target or analyte of interest, the label probe, and the entity capable of generating (or releasing) an activating agent). In one embodiment, e.g., where the linker molecule includes a biotin and a tyramine separated by a spacer, the spacer includes a number of atoms which is greater than 10.

The relative position of the covalent bond-forming reactive group(s) in the linker molecules may vary provided they are effectively positioned relative to the linker molecule binding moiety to provide for both binding to a functionalized detectable label and covalent bond formation with molecules functionalizing the substrate surface. For example, in some embodiments, a linker molecule including a covalent bond forming reactive group(s) includes a covalent bond forming reactive group in a terminal position relative to the linker molecule binding moiety, e.g., as depicted in FIG. 1. Such embodiments may also include one or more covalent bond-forming reactive groups positioned between a terminal end of the molecule and the linker molecule binding moiety.

In other embodiments the linker molecules do not include a terminally positioned covalent bond-forming reactive group but instead include one or more covalent bond-forming reactive groups positioned between a terminal end of the molecule and the linker molecule binding moiety.

In some embodiments, the linker molecules do not have the structure of a naturally occurring molecule, e.g., a naturally occurring nucleic acid or protein molecule. In some embodiments, the covalent bond-forming reactive group(s) of the linker molecules do not have the structure of a covalent bond forming reactive group(s) of a naturally occurring nucleic acid or protein molecule. For example, in some embodiments, the covalent bond-forming reactive group(s) are reactive groups other than tyrosine and thymine.

In some embodiments, the linker molecules include a polymeric structure, e.g., a polymeric spacer structure. In some such embodiments, the covalent bond-forming reactive group(s) include aromatic ring structures. In some embodiments, a suitable linker molecule includes a linker molecule binding moiety, a polymeric spacer structure, and one or more covalent bond-forming reactive groups. Covalent bond-forming reactive groups may include aromatic groups, e.g., phenolic groups. In some embodiments, the aromatic group is tyramine or a tyramine derivative. In other embodiments, the aromatic group is thymine or a thymine derivative.

Where the covalent bond-forming reactive group or groups are aromatic groups, the aromatic groups may, in some embodiments, include a plurality of electron-donating substituents on the aromatic ring, including alkyl and oxyalkyl groups and unsaturated systems.

As with the functionalization of substrate surfaces, covalent bond-forming reactive groups for use in linker molecules may be selected based on the particular entity capable of generating (or releasing) an activating agent which is to be utilized therewith and vice versa. For example, phenolic groups may be selected where the entity capable of generating (or releasing), an activating agent is a peroxidase conjugate, e.g., HRP conjugate, or other entity capable of generating a free radical which results in covalent bond formation between a phenolic group and another covalent bond forming reactive group. Other combinations of entities capable of generating (or releasing) an activating agent and covalent bond-forming reactive groups are known in the art and such may be utilized in connection with the disclosed methods and compositions. For example, one or more glycosidic bonds may be utilized as covalent bond-forming reactive groups in connection with a glycosidase conjugate capable of cleaving the glycosidic bond to expose an aldehyde group which can in turn form a covalent bond with an amino or hydrazide covalent bond forming reactive group.

The linker molecule may include a single participating reactive group or a plurality of participating reactive groups. Where the linker molecules include a plurality of covalent bond-forming reactive groups, the number of covalent bond-forming reactive groups in the molecule may be 2, 3, 4, 5, 6, 7, 8, 9, 10 or more.

In some embodiments, the linker molecules are copolymers containing polymer units with a high concentration of covalent bond-forming reactive groups. For example, in some embodiments, a copolymer is utilized in which the ratio of polymer units containing covalent bond-forming reactive groups to polymer units which do not contain covalent bond-forming reactive groups is at least 1:4, at least 1:3, at least 1:2, at least 1:1, at least 2:1, at least 3:1, at least 4:1, at least 5:1, at least 6:1, at least 7:1, at least 8:1, at least 9:1, or at least 10:1. Suitable linker molecules may include a single linker molecule binding moiety, e.g., a single $1^{st}$ member of a specific binding pair, or a plurality of linker molecule binding moieties, e.g. a plurality of $1^{st}$ members of a specific binding pair. Where the linker molecule includes a plurality of specific binding moieties, the number of specific binding moieties in the linker molecule may be 2, 3, 4, 5, 6, 7, 8, 9, 10 or more. In some embodiments, the linker molecules are copolymers containing a high concentration of linker molecule binding moieties. For example, in some embodiments, a copolymer is provided in which the ratio of monomeric units containing linker molecule binding moieties to monomeric units lacking the linker molecule binding moieties is at least 1:4, at least 1:3, or at least 1:2, at least 1:1, at least 2:1, at least 3:1, at least 4:1, at least 5:1, at least 6:1, at least 7:1, at least 8:1, at least 9:1, or at least 10:1.

Accordingly, it should be understood that a particular linker molecule may include a single covalent bond forming reactive group and a single linker molecule binding moiety, a single covalent bond forming reactive group and a plurality of linker molecule binding moieties, a plurality of covalent bond forming reactive groups and a plurality linker molecule binding moieties (e.g., a plurality of tyramine molecule and a plurality of biotin molecules), or a plurality of covalent bond forming reactive groups and a single linker molecule binding moiety.

Linking molecules may have a structure as set forth in formula (IV) below:

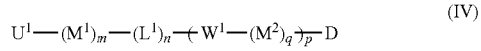
(IV)

wherein:
$L^1$, $W^1$, $M^1$, $M^2$, D, n, p, and q are as described in formula (I); and
$U^1$ is a first member of a specific binding pair or a covalent bond-forming reactive group as defined above for formula (II).

In some embodiments, each instance of $L^2$ and each instance of $L^1$ are independently selected from $C_1$-$C_{24}$ alkylene, heteroatom-containing $C_1$-$C_{24}$ alkylene, $C_2$-$C_{24}$ alkenylene, polyalkylene, and poly(alkylene oxide), any of which may be substituted or unsubstituted.

In some embodiments, $U^1$ is selected from a biotin moiety, a nucleic acid sequence, an antigen, an antibody, an hapten, an avidin or streptavidin moiety, a sugar moiety, a lectin moiety, and an enzyme or apoenzyme.

In some embodiments, $U^1$ is a biotin moiety, such that the linker molecule has the structure of formula (IVa):

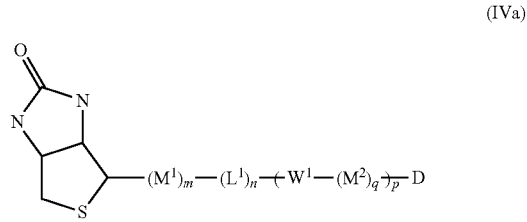
(IVa)

For example, in some embodiments, in formula (I) or (IV), D is *-$M^3$-$Ar^1$, wherein $Ar^1$ is 4-hydroxyphenyl and $M^3$ is substituted heteroatom-containing alkylene (i.e., —C(=O)NH—CH$_2$—CH$_2$—). Furthermore, p is 0 and m and n are both 1. Furthermore, $L_1$ is —(CH$_2$)$_5$— and $M_1$ is —(CH$_2$)$_4$—C(=O)NH—. Alternatively, $L^1$ is —CH$_2$CH$_2$—(OCH$_2$CH$_2$)$_{n1}$—, wherein n1 is an integer from 1 to 30, for example 1, 2, 3, 4, 5, 6, 7, 8, 9, 10, 11, 12, 13, 14, 15, 20, 25, or 30, and the other variables are as previously described.

Also for example, in some embodiments, in formula (I) or (IV), D is *-$M^3$-$Ar^1$, wherein $Ar^1$ is 4-hydroxyphenyl and $M^3$ is substituted heteroatom-containing alkylene (i.e., —C(=O)NH—CH(CO$_2$H)—CH$_2$—). Furthermore, p is 0 and m and n are both 0. Alternatively, m and n are both 1, $L^1$ is —NH—C(=O)—CH$_2$CH$_2$—, and $M^1$ is —C(=O)NH—(CH$_2$CH$_2$O)$_{m1}$—CH$_2$CH$_2$—, wherein m1 is an integer from 1 to 30, for example 1, 2, 3, 4, 5, 6, 7, 8, 9, 10, 11, 12, 13, 14, 15, 20, 25, or 30.

Also for example, in some embodiments, $M^3$ contains a heterocyclic moiety such as a pyrrolidinone moiety. For example, D is *-$M^3$-$Ar^1$, wherein $Ar^1$ is 4-hydroxyphenyl and $M^3$ is

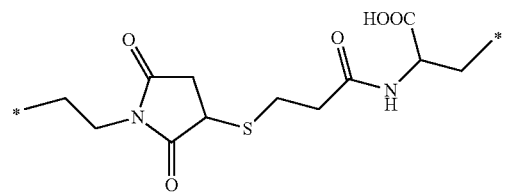 [SMILES: CCCN1C(=O)CC(SCCC(=O)NC(CC)C(=O)O)C1=O]

Furthermore, p is 0 and m and n are both 1. Furthermore, $L^1$ is —NH—C(=O)—(CH$_2$CH$_2$O)—$_1$—CH$_2$CH$_2$—NH—C(=O)—, and $M^1$ is —C(=O)NH—(CH$_2$CH$_2$O)$_{m1}$—CH$_2$CH$_2$—, wherein n1 and m1 are as described above Also for example, in some embodiments, $M^1$ is —NH—C(=O)—(CH$_2$)$_3$—O—(CH$_2$)$_4$—O—(CH$_2$)$_3$—, and the other variables are as previously described.

Figure 3:
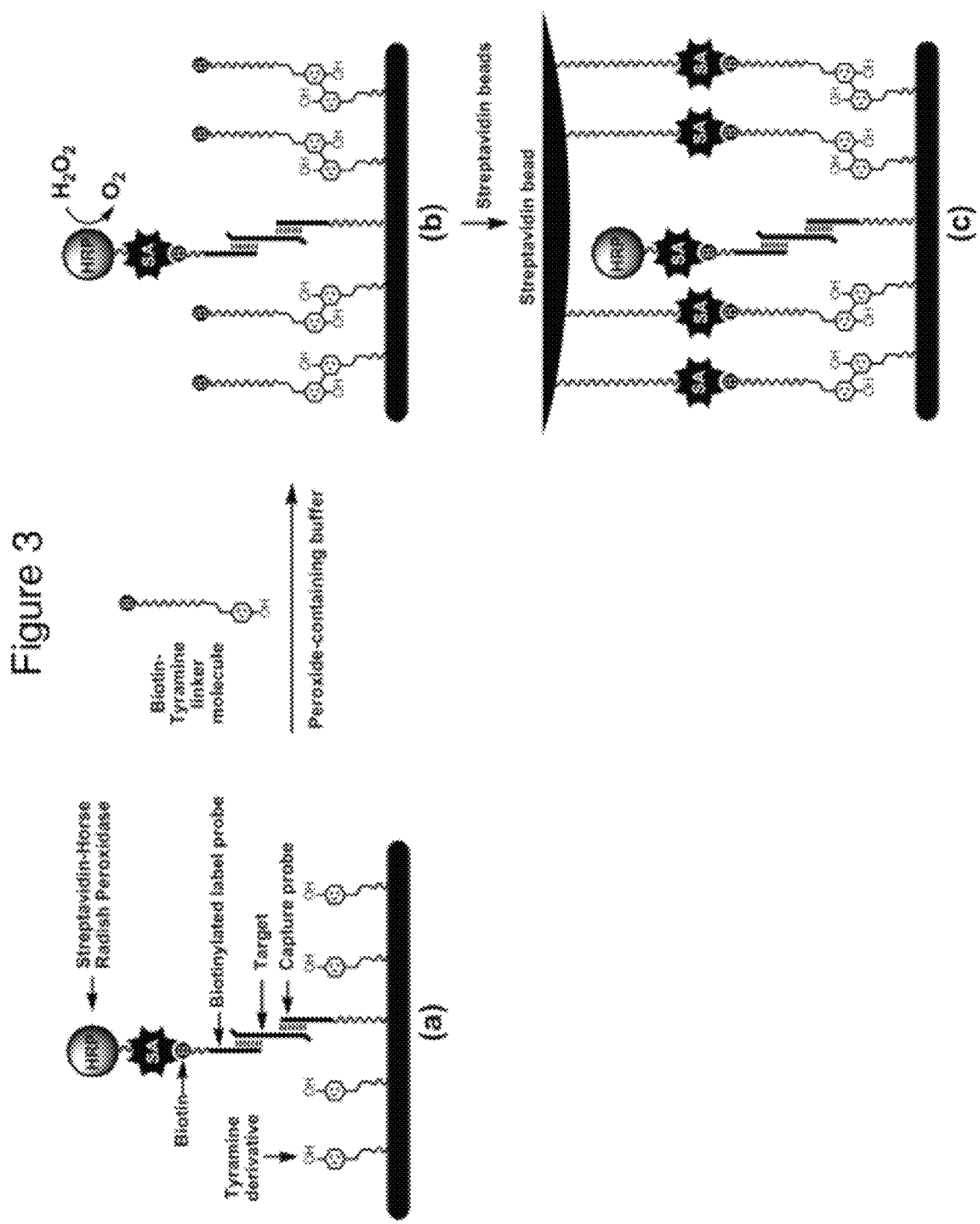
FIG. 3 illustrates one embodiment of the general scheme depicted in FIG. 1, wherein the molecules including $1^{st}$ covalent bond-forming reactive group(s) include tyramine derivatives ((a), (b), and (c)), the label probe is a biotinylated label probe ((a), (b), and (c)), the entity capable of generating (or releasing) an activating agent is a streptavidin-horse radish peroxidase (HRP) enzyme conjugate ((a), (b), and (c)), the linker molecules including $2^{nd}$ covalent bond-forming reactive group(s) are biotin-tyramine conjugates ((b) and (c)), and the functionalized detectable label is a magnetic bead functionalized with streptavidin molecules (c). In (c), the magnetic bead is anchored to the substrate surface via the multiple binding interactions between streptavidin and biotin moieties, where the biotin moieties are covalently linked to the substrate surface.
Figure 4:
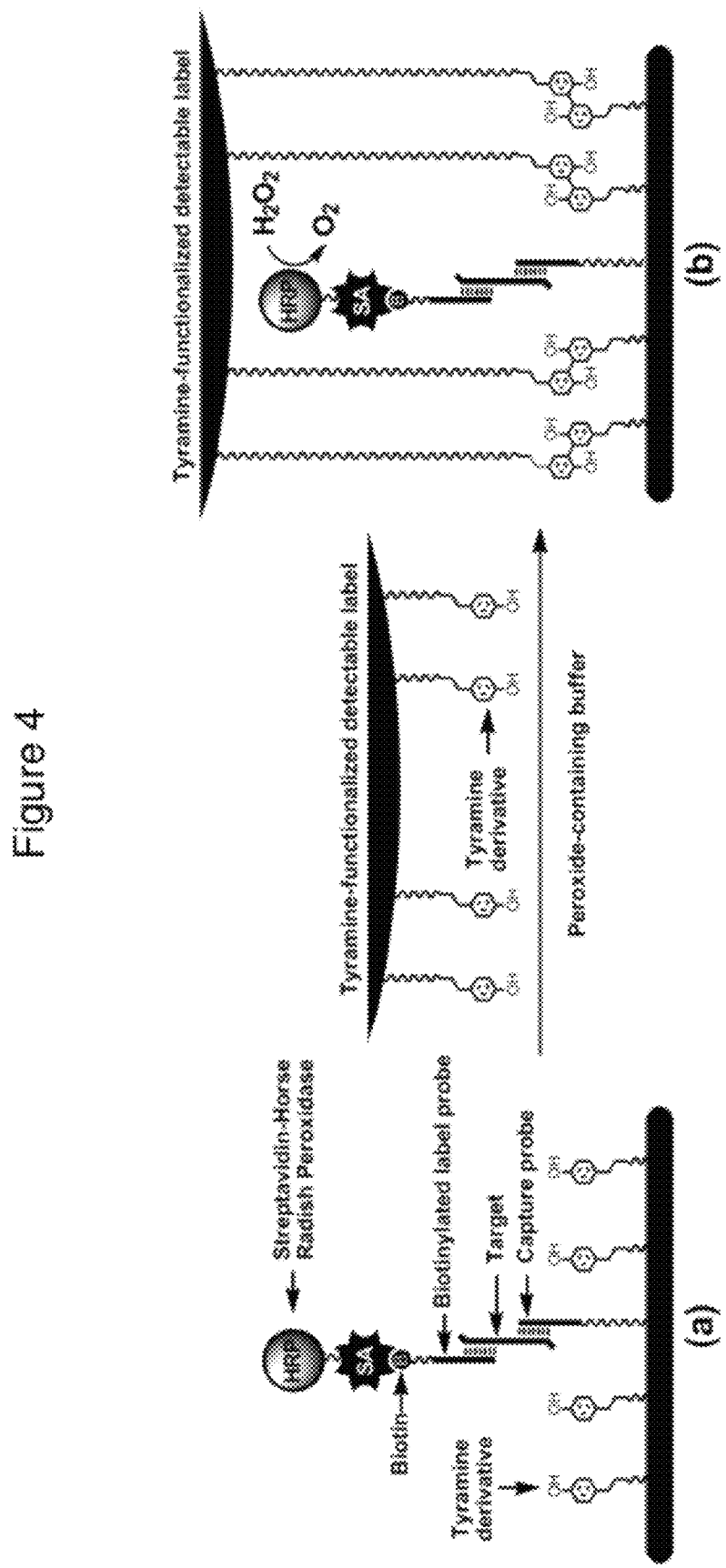
FIG. 4 illustrates one embodiment of the general scheme depicted in FIG. 2, wherein the molecules including $1^{st}$ covalent bond-forming reactive group(s) include tyramine derivatives ((a) and (b)), the label probe is a biotinylated label probe ((a) and (b)), the entity capable of generating (or releasing) an activating agent is a streptavidin-HRP enzyme conjugate ((a) and (b)), and the detectable label functionalized with $2^{nd}$ covalent bond-forming reactive group(s) is a tyramine-functionalized bead (b). In (b), the bead is anchored to the substrate surface via the HRP-activated covalent bond formation between the $1^{st}$ and $2^{nd}$ tyramine moieties.
Figure 5:
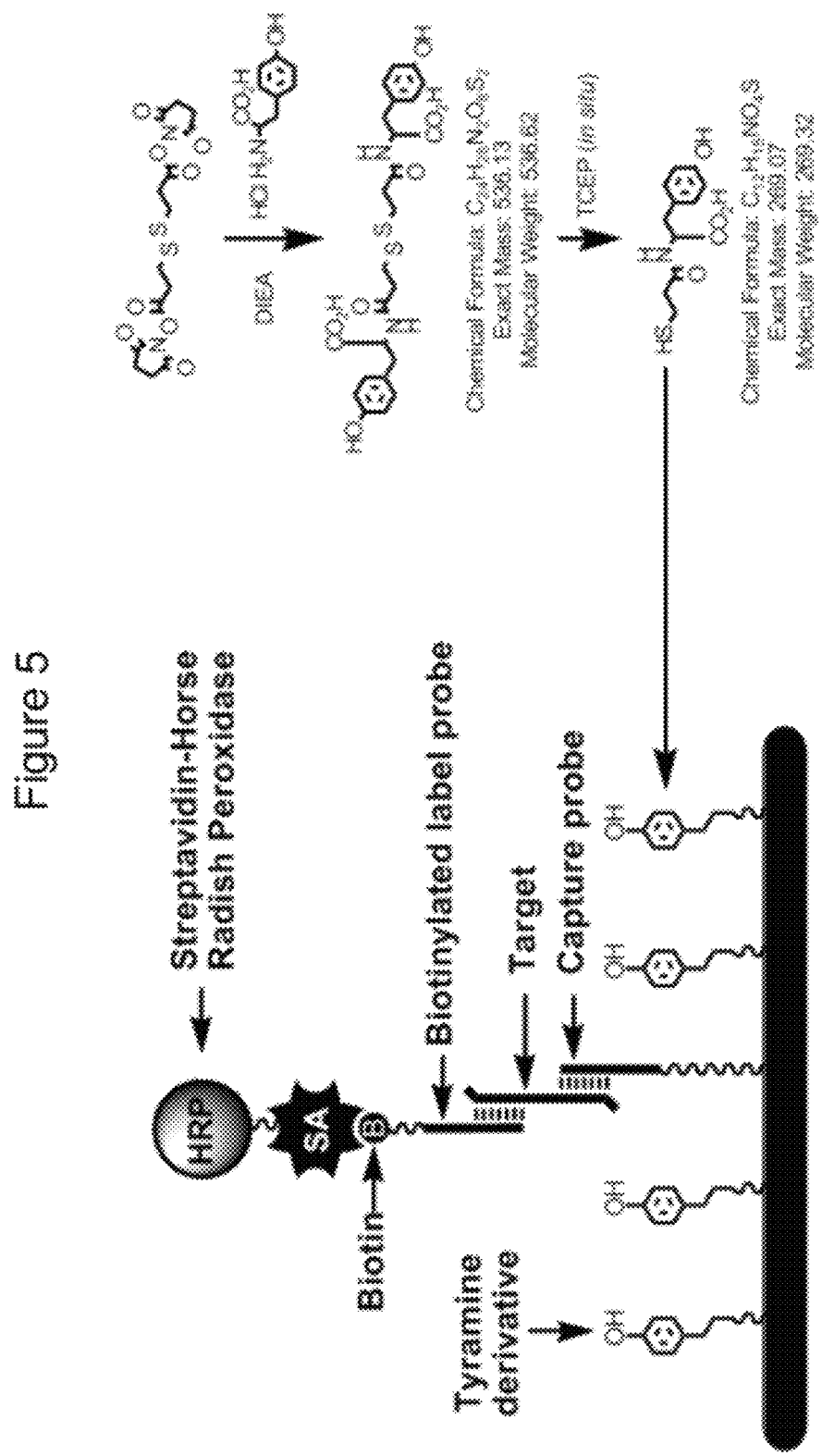
FIG. 5 shows an example of a synthetic scheme for a compound containing a sulfhydryl group and a phenolic group that can be used to functionalize a substrate surface. To enable covalent linking of the depicted compound to the substrate surface, the substrate surface may be first derivatized with maleimide groups, which can react readily with the thiol group.
Figure 8:
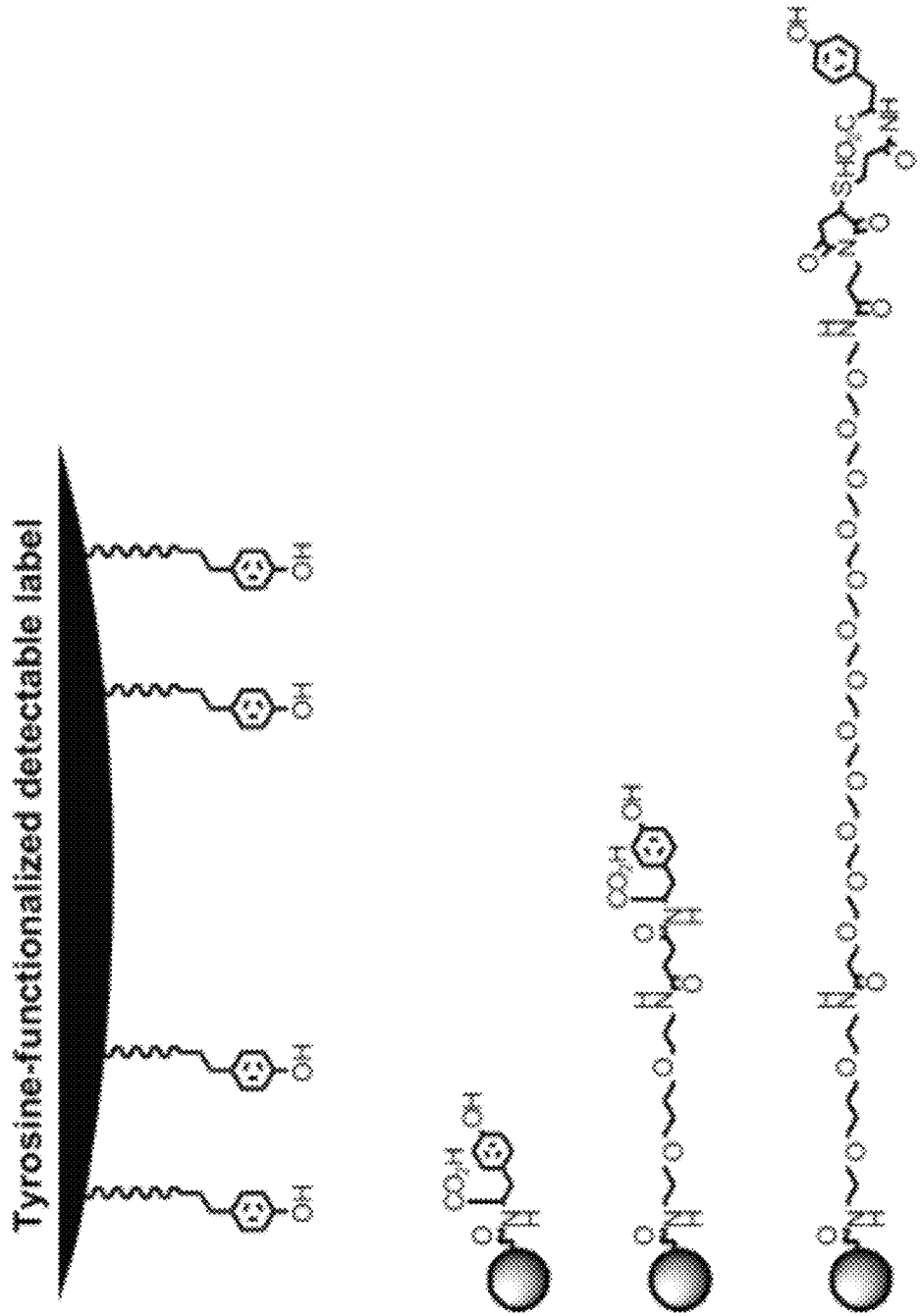
FIG. 8 shows examples of various bead surface phenol group functionalization schemes which may be used to provide functionalized detectable label in accordance with various aspects of the present disclosure. Examples of functionalization schemes with different distances between the bead surface and the tyrosine derivatives are provided.
Figure 9:
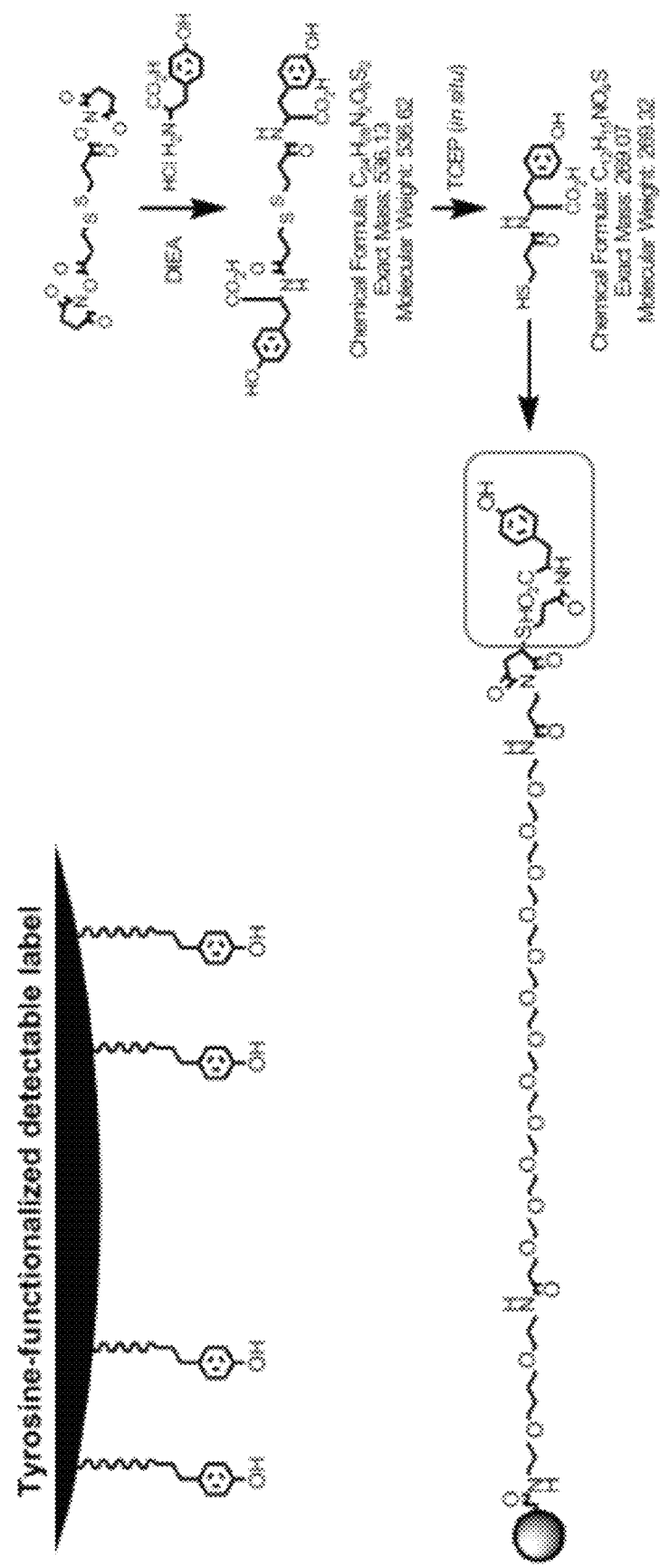
FIG. 9 shows a synthetic scheme for part of the reagent used to generate the longest molecule shown in FIG. 8 spacer.

In one embodiment, a linker molecule according to the present disclosure is a biotin-tyramine conjugate as depicted generally in FIG. 3, wherein biotin is the linker molecule binding moiety and tyramine is the covalent bond-forming reactive group. In one embodiment, a biotin-tyramine conjugate according to the present disclosure has a structure as provided in formula (V) below:

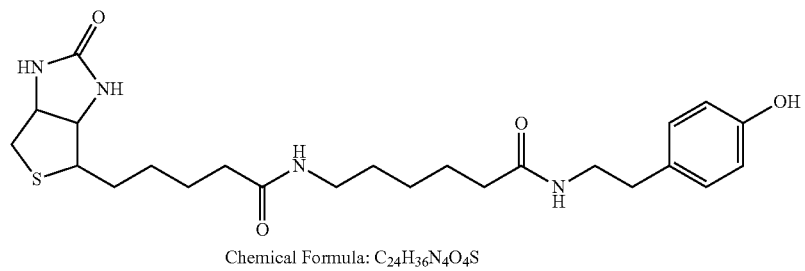

Chemical Formula: C$_{24}$H$_{36}$N$_4$O$_4$S

In another embodiment, a biotin-tyramine conjugate according to the present disclosure has a structure as provided in formula (VI) below:

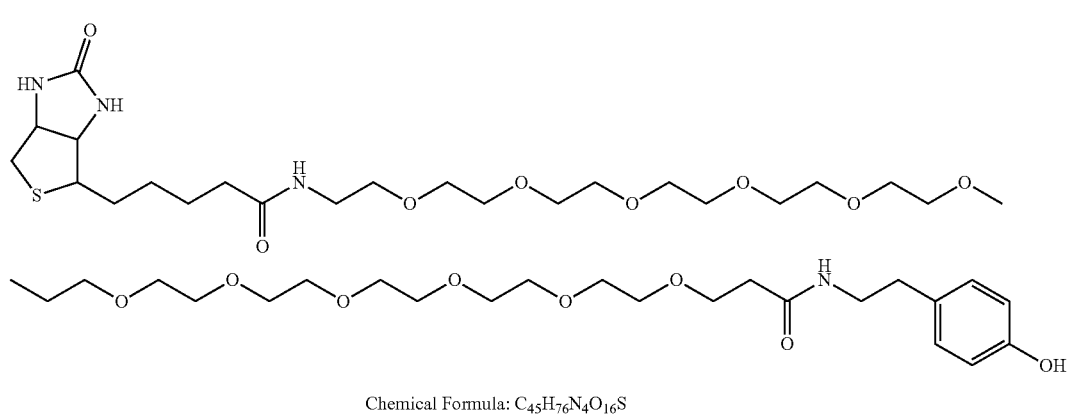

Chemical Formula: C$_{45}$H$_{76}$N$_4$O$_{16}$S

It should be noted that the length of the linker portion of the above molecules which links the specific binding moiety (e.g., biotin moiety) and the covalent bond forming reactive group (e.g., tyramine moiety) may be adjusted to provide a linker molecule having greater or less distance between the specific binding moiety and the covalent bond forming reactive group.

In some embodiments, a linker molecule according to the present disclosure includes one or more phenolic covalent bond forming reactive groups having a structure as set forth in Table 4 (provided subsequently herein). In some embodiments, a linker molecule includes one or more specific binding moieties (e.g. one or more biotin moieties).

Target Molecules and Analytes of Interest

The compositions, methods and kits of the present disclosure may be utilized in connection with the qualitative and/or quantitative detection of any of a wide variety of target molecules or other analytes of interest, e.g., peptides, proteins, nucleic acids, viruses, antibodies or fragments thereof (including single-chain antibodies, Fabs, and the like), whole cells, cellular components, organic and inorganic small molecules, or combinations thereof. Protein targets of interest include, for example, cell surface receptors, signal transduction factors, and hormones. Nucleic acid targets of interest include, for example, DNA and RNA targets. Cellular targets of interest include, for example, mammalian cells (particularly human cells) stem cells, and bacterial cells.

Target-Localized Anchoring of Detectable Label and/or Linker Molecules

The above components find use in methods for detecting the presence, absence and/or amount of a target molecule or other analyte of interest in a sample.

Detection of Functionalized Detectable Labels Using Linker Molecules

One embodiment of a detection method according to the present disclosure is depicted generally in FIG. 1. In this embodiment, a functionalized substrate is combined in a reaction mixture with a sample suspected of containing a target molecule or other analyte of interest. The functionalized substrate includes at least one target-specific capture probe and a plurality of molecules including a 1$^{st}$ covalent bond-forming reactive group(s). The stringency of the reaction conditions may be adjusted and one or more wash steps may be utilized to minimize non-specific binding of the target molecule or other analyte of interest. This can be accomplished by adjusting, for example, the pH, temperature and/or salt concentration of the wash conditions.

To the above reaction mixture, one or more label probes are added. The term "label probe" is used herein to refer to a bifunctional molecule having a 1$^{st}$ specific binding moiety capable of specifically binding at least a portion of a target molecule or other analyte of interest when brought into contact with the target molecule or other analyte of interest under suitable reaction conditions and a 2$^{nd}$ specific binding moiety capable of specifically binding an entity capable of generating (or releasing) an activating agent, when brought into contact with the entity under suitable reaction conditions. The stringency of the reaction conditions may be adjusted and one or more wash steps may be utilized to minimize non-specific binding of the label probe.

An entity capable of generating (or releasing) an activating agent is also added to the reaction mixture. In some embodiments, the entity capable of generating (or releasing) an activating agent is an enzyme conjugate. As used herein, the term "enzyme conjugate" refers to an enzyme capable of catalyzing the formation of a covalent bond between a $1^{st}$ covalent bond-forming reactive group and a $2^{nd}$ covalent bond-forming reactive group and/or activating one or more of the $1^{st}$ covalent bond-forming reactive group and the $2^{nd}$ covalent bond-forming reactive group for covalent bond formation, wherein the enzyme is linked to a binding moiety capable of specifically binding a label probe as described herein. A suitable enzyme for the enzyme conjugate may be selected based on the chemical identity and/or characteristics of the $1^{st}$ and $2^{nd}$ covalent bond-forming reactive groups. Similarly, the $1^{st}$ and $2^{nd}$ covalent bond-forming reactive groups may be selected based on the identity and/or characteristics of the enzyme. Non-limiting examples of enzymes capable of catalyzing covalent bond formation between $1^{st}$ and $2^{nd}$ covalent bond-forming reactive groups, and/or activating one or more of the $1^{st}$ covalent bond-forming reactive group and the $2^{nd}$ covalent bond-forming reactive group for covalent bond formation, include, e.g., peroxidases (e.g., horseradish peroxidase), glycosidases and phosphatases (e.g., alkaline phosphatase).

When the target molecule is present in the sample under suitable reaction conditions, a binding complex results as depicted in FIG. 1(a) wherein the entity capable of generating (or releasing) an activating agent is linked to the substrate surface though a series of linkages resulting from the target-specific capture probe binding to the target molecule or analyte of interest, the target molecule or analyte of interest binding to the label probe, and the label probe binding to the entity capable of generating (or releasing) an activating agent. The stringency of the reaction conditions may be adjusted and one or more wash steps may be utilized to minimize non-specific binding of the entity capable of generating (or releasing) an activating agent.

A plurality of linker molecules as described herein are added to the reaction mixture and suitable reaction conditions are provided such that the entity capable of generating (or releasing) an activating agent catalyzes formation of covalent bonds between the $1^{st}$ covalent bond forming reactive groups of the molecules immobilized on the substrate surface and the $2^{nd}$ covalent bond-forming reactive groups of the linker molecules, and/or activates one or more of the $1^{st}$ covalent bond-forming reactive groups and the $2^{nd}$ covalent bond-forming reactive groups for covalent bond formation. In some embodiments, suitable reaction conditions may require the addition of one or more buffers and/or enzyme substrates. For example, where the entity capable of generating (or releasing) an activating agent is an enzyme conjugate including horseradish peroxidase (HRP), a suitable peroxide-containing buffer is added to the reaction mixture to enable the covalent bond formation reaction. As a result of the target-localized action of the entity capable of generating (or releasing) an activating agent, the linker molecules are covalently bound in a target-localized manner to the substrate surface as shown, for example, in FIG. 1(b) and FIG. 3(b). This results in target-localized deposition of linker molecule binding moieties which provide a plurality of "hooks" for subsequent binding of a suitably functionalized detectable label in a target-localized manner and enable the identification of individual, spatially separated sites where the target is bound.

Addition of detectable label functionalized with molecules having binding moieties specific for the linker molecule binding moieties results in a binding complex as illustrated, for example, in FIG. 1(c) and FIG. 3(c), i.e., a binding complex in which multiple independent linkages serve to anchor the detectable label to the substrate surface in proximity to the target molecule captured on the substrate surface. The stringency of the reaction conditions may be adjusted and one or more wash steps may be utilized to minimize non-specific binding of the functionalized label.

Once the detectable label is anchored to the substrate surface in a target-localized manner, one or more detection systems may be utilized to detect and or visualize the location and/or amount of the detectable label which is indicative of the location and/or amount of immobilized target molecule. The particular method used to detect the anchored detectable label will depend on the type of detectable label utilized. For example, where the detectable label is a fluorescent particle, one or more fluorescence-based detection systems may be utilized. Where the detectable label is a magnetic particle, one or more magnetic sensors may be utilized.

In some embodiments, the detectable label anchored to the substrate surface may be detected using a microscopy system which may or may not utilize specifically detectable characteristics of the detectable label such as fluorescence or magnetic field. For example, in some embodiments, the detectable label anchored to the substrate surface may be detectable by an optical microscopy system based solely on its size. This may be the case, for example, where a detectable particle is used which has a diameter of 0.5 µm or more.

Detection of Functionalized Detectable Labels Without Using Linker Molecules

In another embodiment, an alternative detection method may be utilized. This method is illustrated generally in FIG. 2, with a specific example provided in FIG. 4. As in the method described above, a functionalized substrate is combined in a reaction mixture with a sample suspected of containing a target molecule or analyte of interest. The functionalized substrate includes at least one target-specific capture probe and a plurality of molecules including $1^{st}$ covalent bond-forming reactive groups. The stringency of the reaction conditions may be adjusted and one or more wash steps may be utilized to minimize non-specific binding of the target molecule or analyte of interest.

To the above reaction mixture, one or more label probes are added as described above. The stringency of the reaction conditions may be adjusted and one or more wash steps may be utilized to minimize non-specific binding of the label probe.

An entity capable of generating (or releasing) an activating agent, e.g., an enzyme conjugate, is also added to the reaction mixture as described above. When the target is present in the sample under suitable reaction conditions, a binding complex results as depicted in FIG. 2(a) wherein the entity capable of generating (or releasing) an activating agent is linked to the substrate surface though a series of linkages resulting from the target-specific capture probe binding to the target molecule or analyte of interest, the target molecule or analyte of interest binding to the label probe and the label probe binding to the entity capable of generating (or releasing) an activating agent. The stringency of the reaction conditions may be adjusted and one or more wash steps may be utilized to minimize non-specific binding of the entity capable of generating (or releasing) an activating agent.

Figure 2:
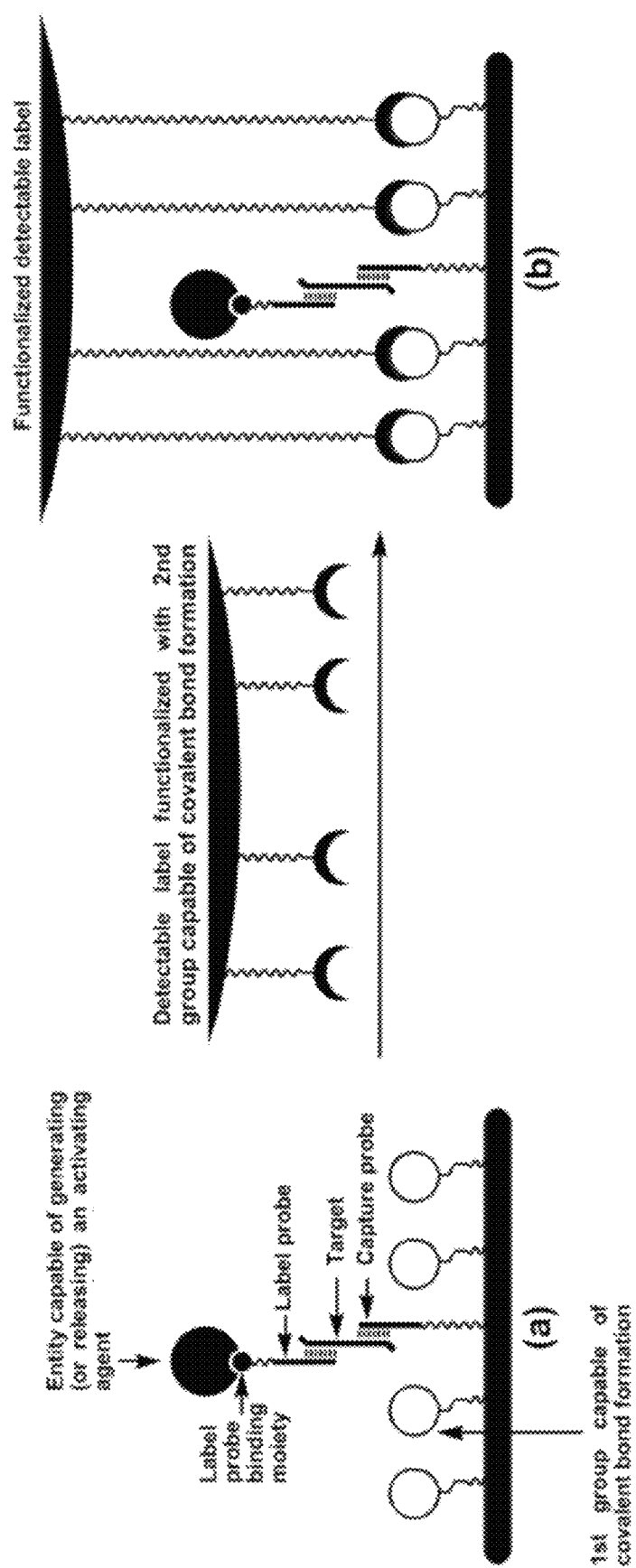
FIG. 2 illustrates binding complexes formed during an alternative target detection method according to the present disclosure as follows: In (a), a complex including a substrate-bound target-specific capture probe, a target molecule, a label probe, and an entity capable of generating (or releasing) an activating agent is formed on the surface of a substrate which includes molecules having $1^{st}$ covalent bond-forming reactive group(s). In the presence of an activating agent generated (or released), a detectable label functionalized with $2^{nd}$ covalent bond-forming reactive group(s) forms covalent bonds with the substrate-bound $1^{st}$ groups, thereby anchoring the functionalized detectable label to the substrate surface in a target-localized manner as shown in (b).

Instead of utilizing linker molecules having $2^{nd}$ covalent bond forming reactive groups, a detectable label functionalized with molecules having $2^{nd}$ covalent bond forming reactive groups is utilized as shown in FIG. 2.

As discussed above, in some embodiments, suitable reaction conditions may require the addition of one or more buffers. For example, where the entity capable of generating (or releasing) an activating agent is an enzyme conjugate including HRP, a suitable peroxide-containing buffer may be added to the reaction mixture to facilitate the covalent bond formation reaction. As a result of the target-localized action of the enzyme, the detectable label is covalently bound in a target-localized manner to the substrate surface as shown, for example, in FIG. 2(b) and FIG. 4(b).

Spatially Separated, Individually Detectable Target Molecule Loci

In some embodiments, one or more reaction condition parameters are adjusted so as to facilitate the deposition of spatially separated, individually detectable target molecule loci. In other words, one or more reaction condition parameters are adjusted such that individual or a very small number of target molecules (e.g., less than about 20, less than about 10, or less than about 5) are present in loci on a substrate surface. As described previously herein, one or more detectable labels are bound in a target-localized manner at each individual target molecule loci to enable detection of the individual target loci. Parameters which may be adjusted to enable detection of spatially separated, individual target loci include the efficiency of target capture by the target-specific capture probes; the level of enzyme activity; the level of reactivity of the covalent bond-forming reactive groups of one or more of the functionalized substrate surface, the detectable label and the linker molecules; the number of specific binding members on the functionalized detectable label; and the number of covalent bond-forming reactive groups on the functionalized detectable label.

In some embodiments, the concentration of target molecules in the sample may be adjusted or the target molecules may be otherwise provided at a concentration which facilitates the formation of spatially separated, individually detectable target loci. For example, in some embodiments, the target molecule concentration is adjusted to provide a target molecule concentration in the sample that results in the formation of target loci in density of no more than one locus per 0.2 square μm of the substrate surface.

In some embodiments, the reaction parameters may be adjusted such that a single detectable label, e.g., a single magnetic particle, is bound at each target molecule loci. Accordingly, in some embodiments target molecule loci as described above may include not more than one target molecule and not more than one detectable label.

Cross-Linking to Strengthen and/or Stabilize a Binding Complex

Once a binding complex has been formed between two or more of the entities described herein, the binding complex can be strengthened and/or stabilized by the introduction of one or more cross-linking agents. It may be desirable, for example, to stabilize a target molecule or analyte of interest bound to a substrate surface via a target-specific capture probe prior to introducing a label probe. Similarly, it may be desirable to stabilize the binding complex formed after the functionalized detectable label has bound to the substrate surface via one or more linker molecule(s).

Cross-Linking Through the Introduction of Covalent Bonds

Cross-linking agents can be introduced to facilitate the formation of covalent bonds between members of a binding complex. Covalent bond energies are usually in the range of 300-400 kJ/mol. Covalent bonds are many folds stronger than the non-covalent binding interactions between a receptor and its ligand, protein and protein, or hybridized double stranded nucleic acids.

A variety of covalent bond-forming reactions suitable for forming covalent bonds between groups or moieties within molecules participating in binding complexes are known in the art including copper-catalyzed azide/alkyne [3+2] cycloaddition "Click Chemistry," azide/DIFO (Difluorinated Cyclooctyne) or copper-free Click Chemistry, azide/phosphine "Staudinger Reaction," azide/triarylphosphine "Modified Staudinger Reaction," and olefin metathesis reactions. These covalent bond-forming reactions may be utilized to introduce covalent bonds to stabilize and/or strengthen the binding complexes as described above. Those of skill in the art will realize that some of these reactions, e.g., copper-catalyzed azide/alkyne [3+2] cycloaddition, require the addition of a catalyst agent to catalyze the binding pair interaction, while others such as the azide/DIFO reaction do not.

There are a variety of agents available in the art which can be used to crosslink between strands of hybridized nucleic acids, between nucleic acids and proteins, and between different protein molecules. Cross-linking reagents of different lengths and combinations of functional groups are commercially available. Alternatively, cross-linking reagents can be designed and synthesized to fit the requirements of a particular cross-linking situation.

For example, glutaraldehyde, a small homo-bifunctional cross linker that has been used extensively to crosslink protein molecules, can be used in connection with the methods and compositions disclosed herein.

In another example, psoralens, a class of photomutagenic compounds that form covalent nucleic acid adducts through photochemical addition, are utilized. The primary reaction is cyclobutane ring formation between the 5,6 double bond of thymidine in DNA and either the 4',5' or 3,4 double bond of the psoralen molecule. Reaction at the 4',5' double bond creates a furan-side monoadduct, which can further react at a site with a flanking pyrimidine on the opposite strand to create an interstrand cross-link. Spielmann et al., *Proc. Natl. Acad. Sci. USA*, 92, 2345-2349 (1995). See also, Okamoto et al., *Org. Lett.* 3; 925-7 (2001), describing the synthesis of a psoralan containing peptide nucleic acid (PNA) from 8-methoxypsoralen. PNA containing a psoralen unit at strand end forms a stable duplex with complementary DNA. Psoralen derivatives with additional functionality have also been synthesized. For example, Saffran et al., *Nucleic Acids Res.*, 16, 7221-31 (1988), describe the synthesis of a biotinylated psoralen (BPsor). BPsor photoreacts with DNA to form interstrand cross-links while providing an additional binding functionality in the form of the biotin moiety which can then bind with a streptavidin molecule.

Crosslinking of hybridized nucleic acid molecules can also be accomplished as described in U.S. Pat. No. 6,800,768 (issued Oct. 5, 2004), wherein non-nucleosidic photoactive coumarin derivatives are incorporated into nucleic acids to enable interstrand crosslinking.

As described in Pendergrast et al., *Proc. Natl. Acad. Sci. USA*, 89, 10287-10291 (1992), photocrosslinking can also be utilized to stabilize binding complexes between proteins and nucleic acids. Specifically, Pedergrast et al. incorporate a photoactivatable crosslinking agent at a single amino acid site within a protein by a two-step procedure consisting of site-directed mutagenesis followed by cysteine-specific chemical modification. First, site-directed mutagenesis is used to introduce a unique solvent-accessible cysteine residue at the position of interest. Then, one derivatizes the resulting protein with a cysteine specific heterobifunctional photoactivatable crosslinking agent, e.g., 4-azidophenacyl bromide. Under defined conditions, reaction of 4-azidophenacylbromide with a protein having a unique solvent-accessible cysteine residue results in complete and highly selective derivatization of the cysteine residue to yield a conjugate of the form [(4-azidophenacyl)-Cys]protein. One then forms the protein-DNA complex and UV irradiation introduces a covalent crosslinker in the protein-DNA complex.

The crosslinking agents can be applied as separate and independent reagents. Alternatively, crosslinking functional groups can be directly conjugated to the linker molecules, capture probes, label probes, substrates, detectable labels, etc. The crosslinking functional group(s) can be activated on command by input such as light, pH changes or specific chemicals applied at a designated point in time. Additionally, the binding moieties and/or linker molecules disclosed herein can be designed to make them suitable for the application of crosslinking agents of choice. For example, conjugation of nucleic acid molecules to target-specific binding moieties including proteins, e.g., antibodies, makes it possible crosslink these binding moieties with a crosslinking reagent that was originally applicable for nucleic acids only. Conversely, conjugating protein or other chemical entities to target-specific binding moieties including nucleic acids makes it possible to broaden the selection of cross linking agents to those originally not applicable for nucleic acids.

EXAMPLES

Example 1

Target Capture on Substrate Functionalized with Covalent Bond Forming Molecules

Two silicon wafer substrates were prepared. The first substrate surface (designated Oligo chip) was functionalized with oligonucleotide capture probes by derivatizing the silicon oxide wafer surface with aminoalkyl silane to impart amino groups on the silicon oxide surface. The amino groups were then converted to maleimide groups using a bifunctional reagent containing a maleimide group and a NHS ester group separated by a PEG spacer. Then, oligonucleotides with a terminal sulfhydryl group were conjugated to the wafer via the maleimide groups. Finally, unreacted maleimide groups were capped with a short PEG-sulfhydryl derivative.

For the second substrate surface (designated W1 chip), the same silicon wafer derivatized with aminoalkyl silane was conjugated with oligonucleotide capture probes. The conjugation process was different than that used for the first substrate, but resulted in a similar extent of conjugation of oligonucleotide probe. In this case, an oligonucleotide with a terminal amino group was prepared. The amino group was subsequently converted to a carboxylic acid group by reaction with succinic anhydride. The terminal carboxylic acid group on the oligonucleotide was then activated by carbodiimide and conjugated to the amino group on the substrate surface. Subsequently, a tyrosine-glutamate copolymer was conjugated onto the substrate surface via the amino groups not taken up by the oligonucleotide conjugation to provide substrate surface-immobilized covalent bond-forming reactive groups. The conjugation of tyrosine-glutamate copolymer was done via carbodiimide activation of the carboxylic acid groups in the copolymer. The tyrosine-glutamate copolymer was prepared with a ratio of approximately 1 tyrosine to 4 glutamate moieties and had an average molecular weight of from about 5 to 20 kD.

Figure 10:
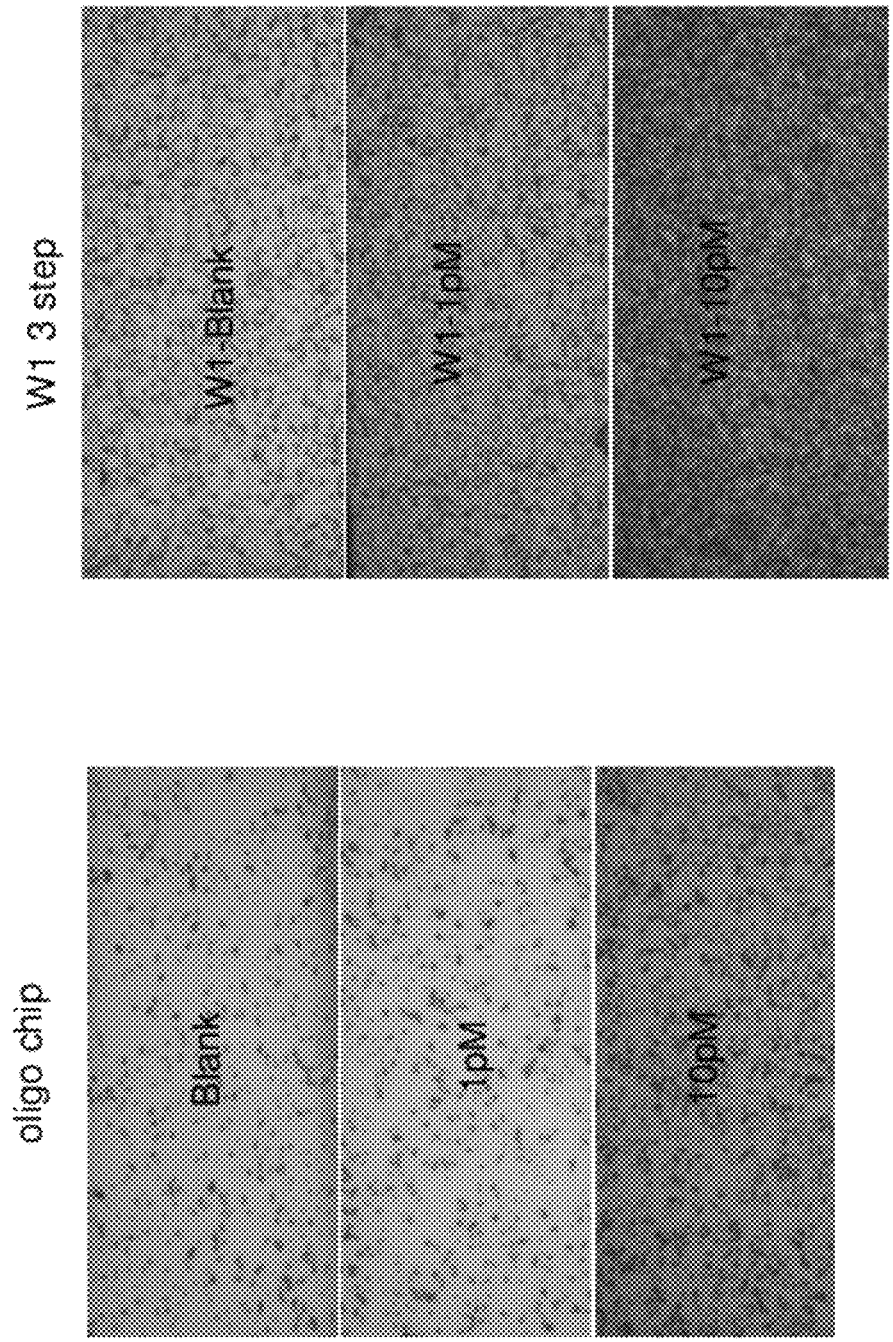
FIG. 10 shows images of the results from the experiment detailed in Example 1, which compares the capture of target molecules on two different substrates using magnetic beads as detectable labels.

In FIG. 10, the capture abilities of the two surfaces to capture the model target were examined. A model target molecule with a segment of sequence complementary to the capture probes conjugated on the substrate surface was applied at the concentrations stated. The model target molecule also contained a second segment with sequence complimentary to an oligonucleotide label probe which was applied later. After the targets were captured on the substrate surfaces by the capture probes, oligonucleotide label probes with a terminal biotin moiety were applied to hybridize to the second segment on the model target molecule. Streptavidinated beads (Invitrogen™, 1 μm) were then applied to bind to the biotinylated labeling probes bound on the model targets.

This experiment was conducted without enzyme-mediated target-localized deposition of linker molecules or anchoring of detectable label. Accordingly, the levels of detection directly reflect the extent to which the substrate surfaces capture the target molecules. As shown in FIG. 10, the Oligo chip and the W1 chip demonstrated similar abilities to capture the model target molecule.

Example 2

Figure 11:
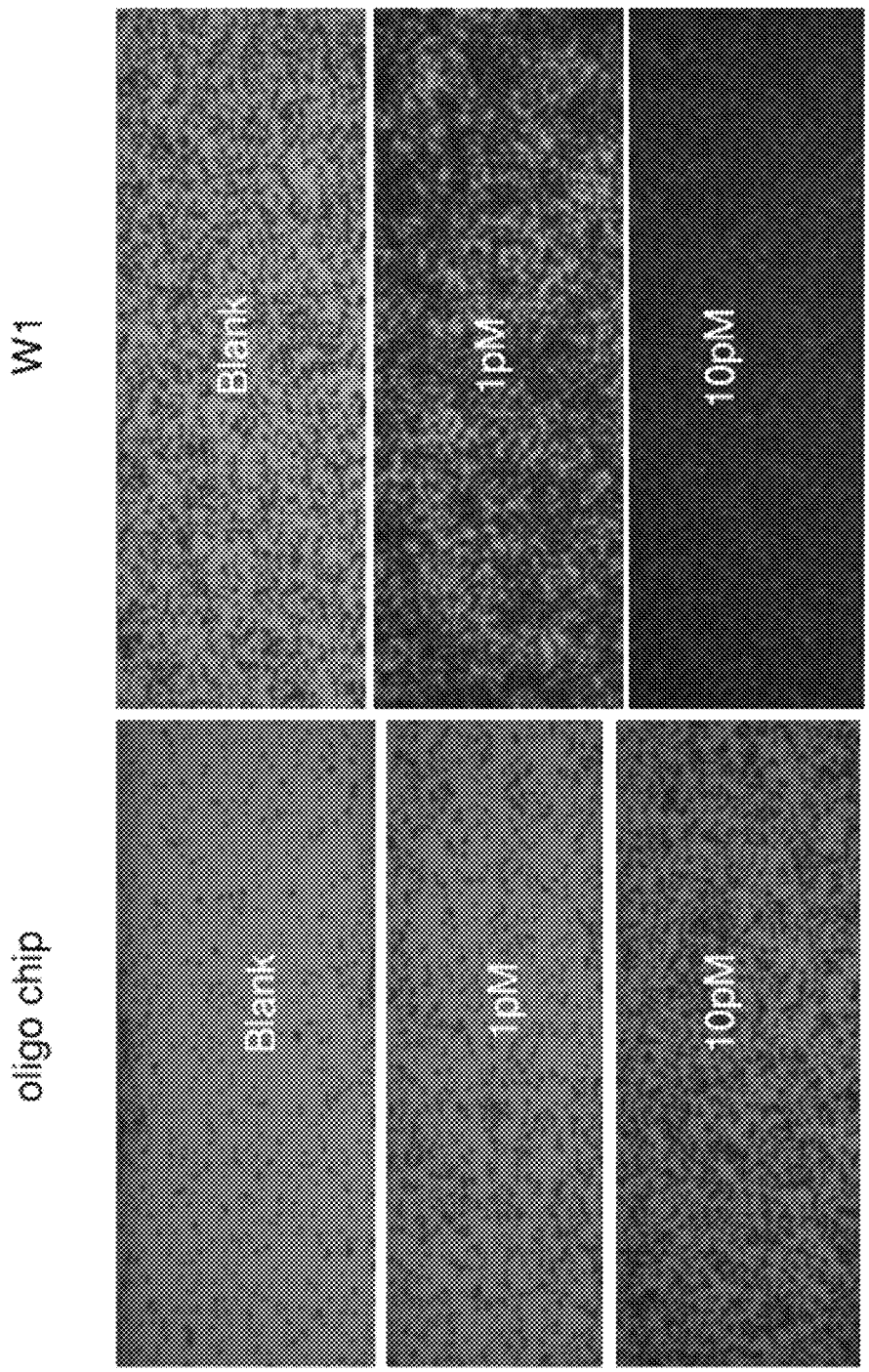
FIG. 11 shows images of the results from the experiment detailed in Example 2, which compares the enzyme-mediated, target-localized deposition of linker molecules on two different substrates using magnetic beads as detectable labels.

Target Capture on Substrate Functionalized with Molecules Including Covalent Bond-Forming Reactive Groups and Target-Localized Deposition of Linker Molecules in the Presence of Enzyme-Generated Activating Agent FIG. 11 shows the levels of detection for both substrates (Oligo chip and W1 chip) with HRP-mediated target-localized deposition of linker molecules. The experiments were done by employing a preformed target complex made up of model target oligonucleotide, biotinylated label probe, and streptavidin-HRP conjugate at the stated concentrations. This allowed the complex to be captured by the capture probes on the substrate surface. Then, by utilizing the free radical generating activity of HRP, linker molecules having structure A of FIG. 13 were covalently linked to tyrosine moieties on the substrate surface. As a result, multiple biotin moieties were deposited in the vicinity of the target molecules immobilized on the substrate surface thereby providing multiple target-localized binding locations for detectable label. Both substrate surfaces were incubated with magnetic, streptavidinated beads approximately 1 μm in diameter (Invitrogen™), and the extent of specific bead binding was determined. The results are depicted in FIG. 11, which shows that the W1 chip modified with tyrosine moieties has enhanced detection sensitivity compared to the Oligo Chip.

Example 3

Surfaces Having Enhanced Linker Molecule Deposition

A variety of substrates modified to include different molecules including covalent bond-forming reactive groups were prepared and tested as described below. The substrate surface naming conventions and functionalization schemes are outlined below in Table 1. To analyze the substrate surfaces, two experiments were conducted. In these experiments, substrate G is a control substrate having no covalent bond-forming reactive groups over and above those present in the capture oligonucleotide. The first experiment measured the ability of the modified substrate surfaces to capture model target molecules. The model targets were applied at various concentrations as indicated in Table 2. Captured targets were labeled with biotinylated oligonucleotides with sequence complementary to a section of the target molecule. The biotinylated oligonucleotide label probes captured on the substrate surfaces via the target molecules were subsequently labeled with streptavidinated alkaline phosphatase and quantified by the dephosphorylation of p-nitrophenyl phosphate (PNPP).

Streptavidin-alkaline phosphatase was added at 1:1000 dilution (Pierce Part #21324, originally 2.8 mg/mL) in PBS.1% Tween and the plate was shaken for 15 min. The chips were washed four times with PBS.1% Tween including moving the chip location in the plate after the third wash to ensure no alkaline-phosphatase was present in the next step of the assay.

1-Step PNPP substrate (Pierce Part #37621) was added to each chip and the plate shaken for exactly 30 min. After 30 min, 50 μL 2N NaOH was added to each well to terminate the reaction. The absorbance at 405 nm was determined for the solution over each chip using DI water as a blank.

The results for this first type of experiment, shown in Table 2, indicate that each of the modified substrates is capable of successfully capturing model target molecules, but at different levels.

TABLE 2

UV Absorbance at 405 nm

| Chip Name | Concentration of Target Molecule | | | |
|---|---|---|---|---|
| | 10 nM | 1 nM | 100 pM | Blank |
| A 6 SA-KT50-H | 0.472 | 0.102 | 0.036 | 0.023 |
| B SA-KT4120-H | 0.475 | 0.158 | 0.051 | 0.020 |
| C SA-K1-H | 0.441 | 0.073 | 0.024 | 0.016 |
| D SA-K15-H | 0.478 | 0.118 | 0.039 | 0.015 |
| E SA-Dend4-H | 0.533 | 0.117 | 0.036 | 0.026 |
| F SA-Dend5-H | 0.435 | 0.099 | 0.029 | 0.022 |
| G SA | 0.336 | 0.054 | 0.018 | 0.019 |
| H SA-10Thy-T | 0.456 | 0.044 | 0.017 | 0.020 |
| 7 SA-C | 0.459 | 0.062 | 0.023 | 0.021 |
| SA-8-T | 0.421 | 0.064 | 0.022 | 0.024 |

The second experiment measured the ability of the modified substrates to form covalent bonds with linker molecules containing phenolic groups in the presence of HRP. The experiment was done by employing a preformed target complex made up of model target oligonucleotide, biotinylated label probe, and streptavidin-HRP conjugate at the stated concentrations. This allowed the complex to be captured by the complementary capture probes on the substrate surface. Then, by utilizing the free radical generating activity of HRP, linker molecules having structure A of FIG. 13 were covalently linked to phenolic or thymine groups on the substrate surface. After the HRP reaction, the biotin moieties on the surface, as a result of linker deposition on the substrate surface, were labeled with streptavidinated alkaline phosphatase and quantified by the dephosphorylation of p-nitrophenyl phosphate.

TABLE 1

| | Molecules Used in Stepwise Substrate Surface Functionalization[a] | | | |
|---|---|---|---|---|
| Chip Name | 1[b] | 2[c] | 3 | 4[d] |
| A 6 SA-KT50-H | SA | Oligo | Poly (Lys, Tyr) hydrobromide Lys:Tyr (1:1), mol wt 50,000-150,000; Sigma part # P4274 | 4-HPAA |
| B SA-KT4120-H | SA | Oligo | Poly (Lys, Tyr) hydrobromide Lys:Tyr (4:1), mol wt 20,000-50,000; Sigma part # P4659 | 4-HPAA |
| C SA-K1-H | SA | Oligo | Poly-L-lysine hydrobromide, mol wt 1000-5000; Sigma part # P0879 | 4-HPAA |
| D SA-K15-H | SA | Oligo | Poly-L-lysine hydrobromide, mol wt 15,000-30,000, Sigma part # P7890 | 4-HPAA |
| E SA-Dend4-H | SA | Oligo | PAMAM[e] dendrimer, ethylenediamine core, generation 4.0 solution: 10 wt. % in methanol; Sigma part # 412449 | 4-HPAA |
| F SA-Dend5-H | SA | Oligo | PAMAM[e] dendrimer, ethylenediamine core, generation 5.0 solution: 5 wt. % in methanol; Sigma part # 536709 | 4-HPAA |
| G SA | SA | Oligo | n/a | n/a |
| H SA-10Thy-T | SA | Oligo-10T | Tyramine; Sigma part # T2879 | n/a |
| 7 SA-C | SA | Oligo | N-(3-(2-(2-(3-aminopropoxy)ethoxy)ethoxy)propyl)-3-(4-hydroxyphenyl)acrylamide[f] | n/a |
| SA-8-T | SA | Oligo | Tyramine; Sigma part # T2879 | n/a |

[a]Following functionalization of the silicon oxide substrate surface with an aminosilane derivative, a series of molecules were covalently bound to the substrate surface in a specific order
[b]SA: Succinic Anhydride Sigma Part #239690
[c]Oligo: 50mer oligonucleotide with 5' amine group; Oligo-10T = 50mer + 10 3'Thymine residues = 60mer oligonucleotide with 5' amine group
[d]4-HPAA: 4-hydroxyphenylaceticacid Sigma Part #H50004
[e]PAMAM: Polyamidoamine
[f]The structure for N-(3-(2-(2-(3-aminopropoxy)ethoxy)ethoxy)propyl)-3-(4-hydroxyphenyl)acrylamide is provided below in formula (VII):
(VII)

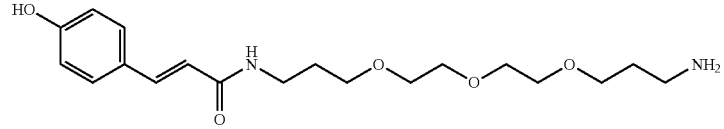 [SMILES: NCCCOCCOCCOCCCNC(=O)/C=C/c1ccc(O)cc1]

The assay conditions to which the chips were subjected are summarized in Table 3 below. The chips were deposited in a 96 well plate. All volumes added to the chip were 100 µL except where stated. The chips were wetted for 10 min in PBS.NaCl.0.1% Tween.sDNA13 (where NaCl denotes that an additional 0.5 M NaCl was added to the PBS buffer, and sDNA13 denotes sacrificial DNA (a 50 mer oligonucleotide at 10 nM)).

The target complex at a given concentration was added to the chips and the plate shaken for 30 min. The chips were then washed three times.

Figure 13:
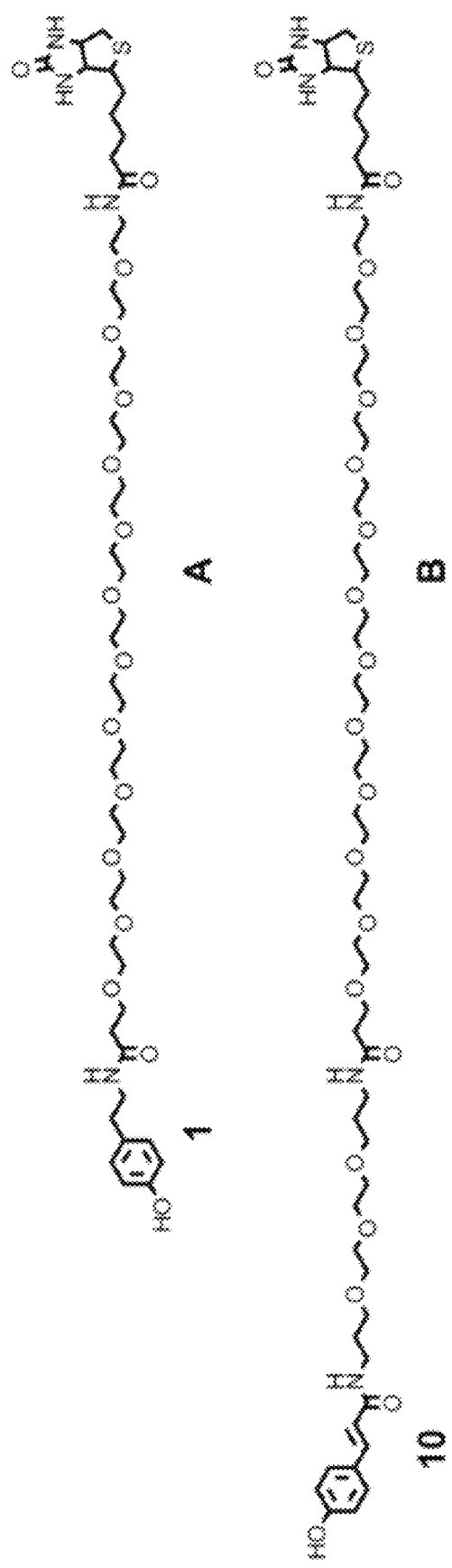
FIG. 13(A-B) shows two linker molecules including a biotin moiety and aromatic groups separated by spacers of differing length.

The linker molecule having structure A of FIG. 13 was added to the chips in SPB.NaCl.0.05% Tween and the plate remained static for 15 min (i.e. no shaking). (SPB denotes Stable Peroxide Buffer (Pierce Part #34062, NaCl denotes that an additional 0.5 M NaCl was added to the SPB buffer, and the Tween used in this solution is Tween 20, low peroxide, low carbonyls, Sigma Aldrich Part #P6585)

The chips were washed once with PBS.1% SDS. The chips were then left standing in PBS.1% SDS for 10 min.

The chips were washed five times with PBS.1% Tween including moving the chip location in the plate after the fourth wash to ensure no SDS is present in the next step of the assay.

Streptavidin-alkaline phosphatase was added at 1:1000 dilution (Pierce Part #21324, originally 2.8 mg/mL) in PBS.1% Tween and the plate was shaken for 15 min. The chips were washed four times with PBS.1% Tween including moving the chip location in the plate after the third wash to ensure no alkaline-phosphatase was present in the next step of the assay.

1-Step PNPP substrate (Pierce Part #37621) was added to each chip and the plate shaken for exactly 30 min. After 30 min, 50 µL 2N NaOH was added to each well to terminate the reaction. The absorbance at 405 nm was determined for the solution over each chip using DI water as a blank.

TABLE 3

| Operation | Duration | Details | Buffer |
|---|---|---|---|
| Wet Chip | 10 min | | PBS.NaCl.0.1% T.sDNA13 |
| Complex | 30 min | | PBS.NaCl.0.1% T.sDNA13 |
| Wash 3X | | | PBS.NaCl.0.1% T.sDNA13 |
| B-T Static | 15 min | 0.1 mM | SPB.NaCl.0.05% T |
| Wash 1X | | | PBS.1% SDS |
| Denature | 10 min | | PBS.1% SDS |
| Wash 5X | | Move locn | PBS.1% T |
| SA-AP | 15 min | 1:1000 diln | PBS.1% T |
| Wash 4X | | Move locn | PBS.1% T |
| PNPP | 30 min | 100 uL | |
| 2N NaOH | | 50 uL | |

As shown in Table 4, where substrate G (oligo) is a control substrate having no covalent bond-forming reactive groups over and above those present in the capture oligonucleotide, substrates modified with additional covalent bond-forming reactive groups over and above those present in the capture oligonucleotide display increased enzyme-mediated deposition of the biotinylated linker molecules on the substrate surface.

TABLE 4

| | UV Absorbance at 405 nm | | | | | |
|---|---|---|---|---|---|---|
| | Concentration of Target Complex | | | | | |
| Chip Name | 100 pM | 10 pM | 1 pM | 100 fM | 10 fM | Blank |
| A 6 SA-KT50-H | 1.111 | 1.109 | 0.301 | 0.081 | 0.048 | 0.041 |
| B SA-KT4120-H | 1.007 | 0.894 | 0.570 | 0.304 | 0.072 | 0.056 |
| C SA-K1-H | 0.957 | 0.411 | 0.089 | 0.036 | 0.022 | 0.022 |
| D SA-K15-H | 0.889 | 0.714 | 0.231 | 0.098 | 0.038 | 0.035 |
| E SA-Dend4-H | 0.941 | 0.695 | 0.238 | 0.069 | 0.029 | 0.026 |
| F SA-Dend5-H | 0.931 | 0.770 | 0.198 | 0.070 | 0.026 | 0.016 |
| G SA (oligo) | 0.297 | 0.189 | 0.052 | 0.022 | 0.028 | 0.034 |
| H SA-10Thy-T | 0.401 | 0.234 | 0.039 | 0.021 | 0.017 | 0.015 |
| 7 SA-C | 0.590 | 0.275 | 0.129 | 0.024 | 0.018 | 0.025 |
| SA-8-T | 0.591 | 0.286 | 0.166 | — | — | 0.022 |

Figure 12:
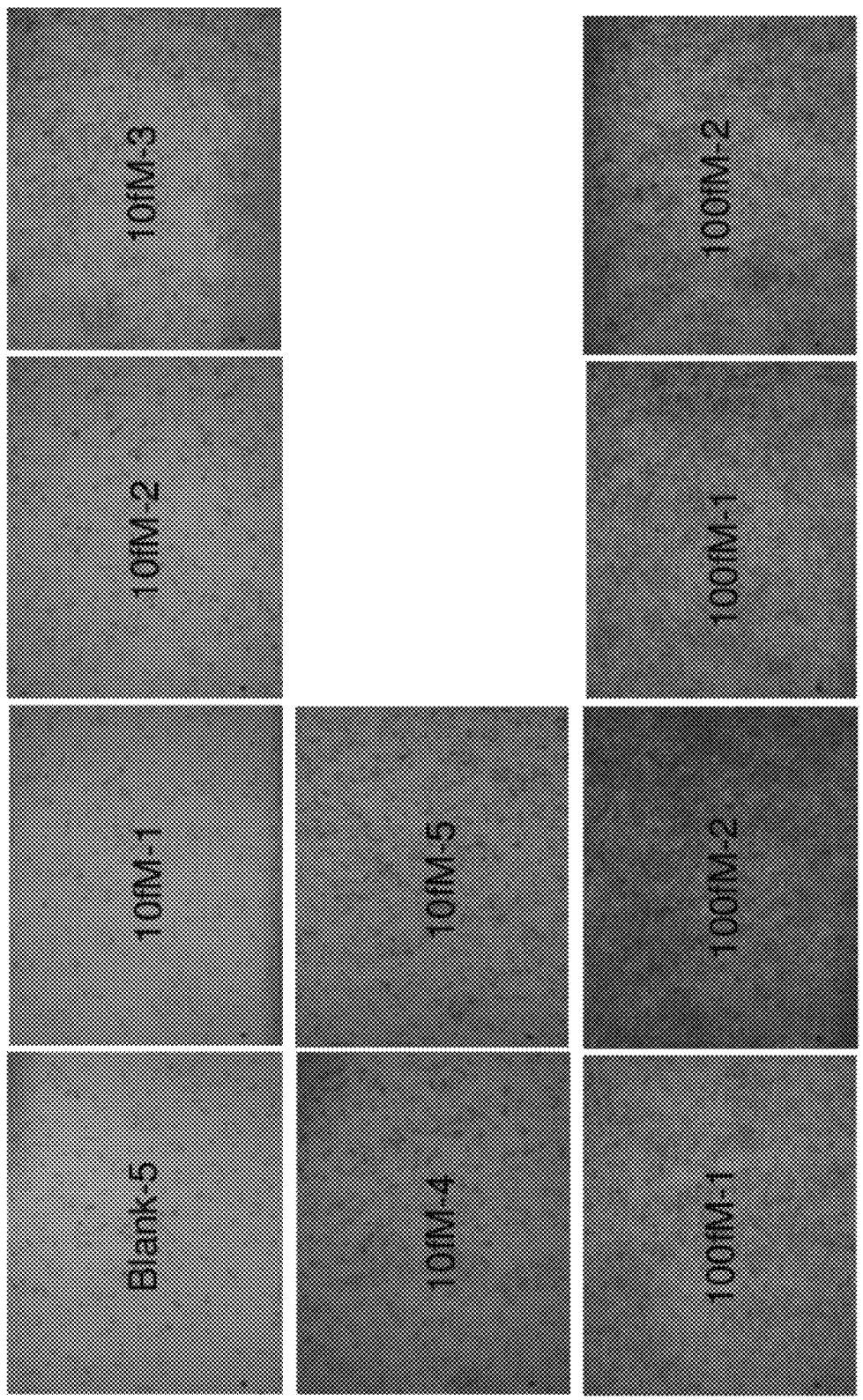
FIG. 12 shows image results for Example 3 in which testing of the SA-8-T functionalized substrate surface was conducted to determine detection limits using magnetic beads as labels.

Further testing of select modified substrate surfaces was conducted to determine limits of detection using magnetic beads as detectable labels. Specifically, the SA-8-T modified substrate was tested utilizing the linker molecule depicted in FIG. 13 (Structure A) and fpm streptavidinated magnetic beads (Invitrogen™). The results, provided in FIG. 12, demonstrate detection limits in the 10 fM range indicating improvement over the detection limit of substrate G (oligo chip) with no additional covalent forming groups other than those present in the oligo capture probes.

Example 4

Preparation and Testing of Linker Molecules

A variety of linker molecules including covalent bond-forming reactive groups were synthesized and tested for their reactivity in the HRP-mediated covalent bond forming reaction with other groups capable of participating in the covalent bond forming reaction on the substrate surface. Linker molecules having different covalent bond-forming reactive groups were prepared using one of the two biotin-PEG spacer structures depicted in FIG. 13, sections A and B, and provided below in formulas (VIII) and (IX) respectively.

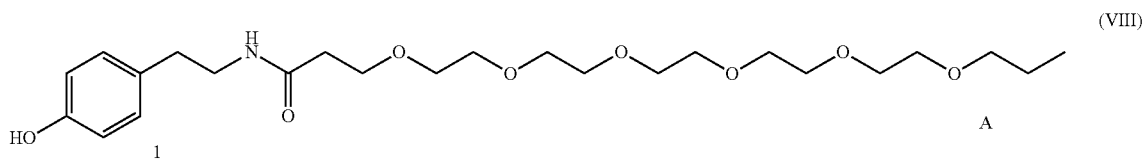

(VIII)

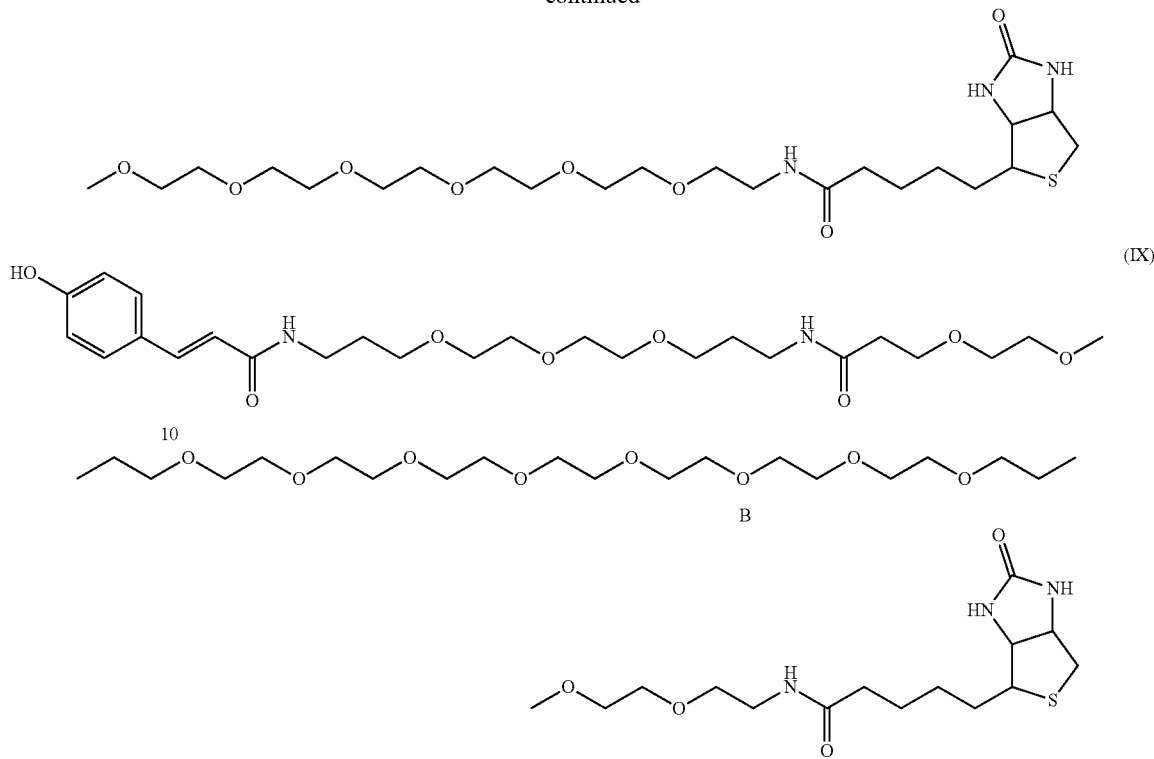

(IX)

Chemical structures for the phenolic ring portions of eighteen selected linker molecules are depicted in FIG. 14. Full chemical names for the linking molecules are provided in Table 5 below. Compounds 1, 2 and 5 are based on the biotin-PEG spacer structure shown in FIG. 13 (A). Compounds 6-14 and 16-18 are based on the biotin-PEG spacer structure shown in FIG. 13 (B). Compounds 3, 4 and 5 were not synthesized, but are prophetic examples based on the structure shown in FIG. 13(B).

TABLE 5

| Number | Full Chemical Name |
|---|---|
| 1 | N-(4-hydroxyphenethyl)-1-(5-(2-oxohexahydro-1H-thieno[3,4-d]imidazol-4-yl)pentanamido)-3,6,9,12,15,18,21,24,27,30,33,36-dodecaoxanonatriacontan-39-amide |
| 2 | N-(1-carboxylic acid-2-(4-hydroxyphenyl)ethyl)-1-(5-(2-oxohexahydro-1H-thieno[3,4-d]imidazol-4-yl)pentanamido)-3,6,9,12,15,18,21,24,27,30,33,36-dodecaoxanonatriacontan-39-amide |
| 3 | N-(15,55-dioxo-59-(2-oxohexahydro-1H-thieno[3,4-d]imidazol-4-yl) 4,7,10,18,21,24,27,30,33,36,39,42,45,48,51-pentadecaoxa-14,54-diazanonapentacontyl)-4-hydroxybenzamide |
| 4 | N-(15,55-dioxo-59-(2-oxohexahydro-1H-thieno[3,4-d]imidazol-4-yl)-4,7,10,18,21,24,27,30,33,36,39,42,45,48,51-pentadecaoxa-14,54-diazanonapentacontyl)-3-hydroxybenzamide |
| 5 | N-(15,55-dioxo-59-(2-oxohexahydro-1H-thieno[3,4-d]imidazol-4-yl)-4,7,10,18,21,24,27,30,33,36,39,42,45,48,51-pentadecaoxa-14,54-diazanonapentacontyl)-2-hydroxybenzamide |
| 6 | N-(15,55-dioxo-59-(2-oxohexahydro-1H-thieno[3,4-d]imidazol-4-yl)-4,7,10,18,21,24,27,30,33,36,39,42,45,48,51-pentadecaoxa-14,54-diazanonapentacontyl)-4-hydroxy-3-methoxybenzamide |
| 7 | N-(1-(4-hydroxyphenyl)-2-oxo-7,10,13-trioxa-3-azahexadecan-16-yl)-1-(5-(2-oxohexahydro-1H-thieno[3,4-d]imidazol-4-yl)pentanamido)-3,6,9,12,15,18,21,24,27,30,33,36-dodecaoxanonatriacontan-39-amide |
| 8 | N-(1-(3-hydroxyphenyl)-2-oxo-7,10,13-trioxa-3-azahexadecan-16-yl)-1-(5-(2-oxohexahydro-1H-thieno[3,4-d]imidazol-4-yl)pentanamido)-3,6,9,12,15,18,21,24,27,30,33,36-dodecaoxanonatriacontan-39-amide |
| 9 | N-(1-(2-hydroxyphenyl)-2-oxo-7,10,13-trioxa-3-azahexadecan-16-yl)-1-(5-(2-oxohexahydro-1H-thieno[3,4-d]imidazol-4-yl)pentanamido)-3,6,9,12,15,18,21,24,27,30,33,36-dodecaoxanonatriacontan-39-amide |
| 10 | N-(17-(4-hydroxyphenyl)-15-oxo-4,7,10-trioxa-14-azaheptadec-16-enyl)-1-(5-(2-oxohexahydro-1H-thieno[3,4-d]imidazol-4-yl)pentanamido) 3,6,9,12,15,18,21,24,27,30,33,36-dodecaoxanonatriacontan-39-amide |
| 11 | N-(17-(4-hydroxy-3-methoxyphenyl)-15-oxo-4,7,10-trioxa-14-azaheptadec-16-enyl)-1-(5-(2-oxohexahydro-1H-thieno[3,4-d]imidazol-4-yl)pentanamido)-3,6,9,12,15,18,21,24,27,30,33,36-dodecaoxanonatriacontan-39-amide |

TABLE 5-continued

| Number | Full Chemical Name |
|---|---|
| 12 | N-(17-(3,4-dihydroxyphenyl)-15-oxo-4,7,10-trioxa-14-azaheptadec-16-enyl)-1-(5-(2-oxohexahydro-1H-thieno[3,4-d]imidazol-4-yl)pentanamido)-3,6,9,12,15,18,21,24,27,30,33,36-dodecaoxanonatriacontan-39-amide |
| 13 | N-(17-(2-hydroxyphenyl)-15-oxo-4,7,10-trioxa-14-azaheptadec-16-enyl)-1-(5-(2-oxohexahydro-1H-thieno[3,4-d]imidazol-4-yl)pentanamido) 3,6,9,12,15,18,21,24,27,30,33,36-dodecaoxanonatriacontan-39-amide |
| 14 | N-(17-(4-aminophenyl)-15-oxo-4,7,10-trioxa-14-azaheptadec-16-enyl)-1-(5-(2-oxohexahydro-1H-thieno[3,4-d]imidazol-4-yl)pentanamido)-3,6,9,12,15,18,21,24,27,30,33,36-dodecaoxanonatriacontan-39-amide |
| 15 | N-(4-aminophenethyl)-1-(5-(2-oxohexahydro-1H-thieno[3,4-d]imidazol-4-yl)pentanamido)-3,6,9,12,15,18,21,24,27,30,33,36-dodecaoxanonatriacontan-39-amide |
| 16 | N-(15,55-dioxo-59-(2-oxohexahydro-1H-thieno[3,4-d]imidazol-4-yl)-4,7,10,18,21,24,27,30,33,36,39,42,45,48,51-pentadecaoxa-14,54-diazanonapentacontyl)-6-hydroxy-2-naphthamide |
| 17 | N-(15,55-dioxo-59-(2-oxohexahydro-1H-thieno[3,4-d]imidazol-4-yl)-4,7,10,18,21,24,27,30,33,36,39,42,45,48,51-pentadecaoxa-14,54-diazanonapentacontyl)-2-hydroxynicotinamide |
| 18 | N-(15,55-dioxo-59-(2-oxohexahydro-1H-thieno[3,4-d]imidazol-4-yl)-4,7,10,18,21,24,27,30,33,36,39,42,45,48,51-pentadecaoxa-14,54-diazanonapentacontyl)-3-hydroxypicolinamide |

Compound 1 provides a basic linker molecule structure based on the tyramine ring and biotin moiety linked via a PEG spacer. Compound 2 is based on a tyrosine structure with a free carboxylic acid in close proximity to the aromatic ring. To investigate the reactivity/efficiency of the linker molecules in an enzyme-mediated covalent bond forming reaction, a series of linker molecules with different electronic properties were designed and synthesized. Linker molecules 3, 4 and 5 were not synthesized, but were designed based on the structure shown in FIG. 4(B). In general, reactivity of the linker molecule appears to be increased by adding electron-donating substituents to the aromatic ring, which increases the electron density of the aromatic ring and consequently increases the electron density at the reaction center, i.e. the phenolic or aniline group. Linker molecules 3-6 are based on benzoic acid. Linker molecules 7-9 are based on phenylacetic acid, which distances the potentially electron-withdrawing amide group from the ring structure. Linker molecules 10-13 are based on coumaric acid, ferulic acid, caffeic acid, and cinnamic acid respectively. Without wishing to be bound by any particular theory, the unsaturated system in linker molecules 10-13 may donate electron density to the ring, thereby increasing the reactivity at the reaction center. As the relative ring position of the reactive center and other ring-substituents may also have an effect on reactivity, linker molecules 3-13 were prepared to include the reactive phenolic centers at different ring positions relative to other substituents. Linker molecules 10 and 14, and 1 and 15 provide direct comparisons of a phenolic versus an aniline group as the reactive center. Linking molecules 16, 17, and 18 are "wild-card" electron-rich systems for comparison.

Several of the above linker molecules were tested in enzyme-mediated covalent bond forming reactions with substrates denoted SA-8-T described above and a substrate denoted GT8-T, where the substrate surface functionalization schemes for both SA-8-T and GT-8-T are outlined in Table 6.

TABLE 6

| | Molecules Used in Stepwise Substrate Surface Functionalization[a] | | |
|---|---|---|---|
| Chip Name | 1 | 2[b] | 3 |
| SA-8-T | Succinic anhydride | Oligo | Tyramine, Sigma part # T2879 |
| GT-8-T | Poly(Glu, Tyr) sodium salt, Glu:Tyr(4:1), mol wt 20,000-50,000, Sigma part # P0275 | Oligo | Tyramine, Sigma part # T2879 |

[a]Following functionalization of the silicon oxide substrate surface with an aminosilane derivative, a series of molecules were covalently bound to the substrate surface in a specific order.
[b]Oligo: 50mer oligonucleotide with 5' amine group.

The assay conditions to which the SA8-T and GT8-T chips were subjected were as described above in connection with Table 3. The results for linker molecules 7, 10, 11, 12, 13, 15 (FIG. 14 and Table 5) and the linker molecule having structure A of FIG. 13 (denoted B-T in the tables) with the SA-8-T substrate are provided in Table 7 below. The results of comparing linker molecule B-T and linker molecule 10 on the SA-8-T chip and the GT-8-T chip are shown in Table 8 below.

TABLE 7

| Concentration of Target Complex | Crosslinker | | | | | | |
|---|---|---|---|---|---|---|---|
| | B-T | 7 | 10 | 11 | 12 | 13 | 15 |
| 10 nM | 0.362 | 0.222 | 0.436 | 0.395 | 0.167 | 0.081 | 0.144 |
| 1 nM | 0.274 | 0.061 | 0.397 | 0.227 | 0.074 | 0.026 | 0.036 |
| Blank | 0.014 | 0.038 | 0.018 | 0.015 | 0.036 | 0.016 | 0.028 |

TABLE 8

| | Chips and Crosslinker | | | |
|---|---|---|---|---|
| | SA-8-T | | GT-8-T | |
| Concentration of Target Complex | B-T | 10 | B-T | 10 |
| 10 nM Complex | 0.431 | 0.731 | 0.343 | 0.663 |
| 1 nM Complex | 0.258 | 0.417 | 0.053 | 0.259 |
| 100 pM Complex | 0.106 | 0.215 | 0.018 | 0.055 |

TABLE 8-continued

| | Chips and Crosslinker | | | |
| --- | --- | --- | --- | --- |
| | SA-8-T | | GT-8-T | |
| Concentration of Target Complex | B-T | 10 | B-T | 10 |
| 10 pM Complex | 0.018 | 0.053 | 0.013 | 0.016 |
| Blank | 0.024 | 0.015 | 0.014 | 0.019 |

Each of the above linker molecules provided measurable levels of target complex detection at nanomolar levels of target complex, with linker molecule 10 also demonstrating measurable detection at the picomolar level.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A reaction mixture comprising:
a functionalized substrate comprising
   a supporting material;
      one or more target-specific capture probes bound to the surface of the supporting material, wherein each target-specific capture probe is capable of specifically and non-covalently binding to a target molecule analyte; and
      a plurality of molecules bound to the surface of the supporting material, other than the one or more target-specific capture probes, wherein each of the plurality of molecules comprises a first covalent bond-forming reactive group; and
      a plurality of functionalized detectable label particles, wherein each of the functionalized detectable label particles comprises a plurality of molecules bound to the surface of a detectable label particle to provide the functionalized detectable label particle, wherein each of the plurality of molecules bound to the surface of the detectable label particle comprises a second covalent bond forming reactive group, wherein the first covalent bond-forming reactive group is capable of forming a covalent bond with the second covalent bond-forming reactive group, and wherein the plurality of functionalized detectable label particles do not have binding affinity for the target molecule analyte.

2. The reaction mixture of claim 1, further comprising the target molecule analyte specifically bound to one of the one or more target-specific capture probes.

3. The reaction mixture of claim 2, further comprising a label probe specifically bound to the target molecule analyte.

4. The reaction mixture of claim 3, further comprising an enzyme conjugate specifically bound to the label probe.

5. The reaction mixture of claim 4, wherein a functionalized detectable label particle of the plurality of functionalized detectable label particles is linked via multiple covalent bonds to the surface of the supporting material, in proximity to the target molecule analyte specifically bound to one of the one or more target-specific capture probes, via interaction of the first covalent bond forming reactive groups with the second covalent bond forming reactive groups.

6. The reaction mixture of claim 5, comprising a plurality of spatially separated, individually detectable target loci.

7. The reaction mixture of claim 5, wherein the target molecule-analyte is present in the reaction mixture at a concentration of less than about 100 fM.

8. The reaction mixture of claim 5, wherein the target molecule-analyte is present in the reaction mixture at a concentration of about 0.1 fM to about 100 fM.

9. A reaction mixture comprising:
a functionalized substrate comprising
   a supporting material;
   one or more target-specific capture probes bound to the surface of the supporting material, wherein each target-specific capture probe is capable of specifically and non-covalently binding to a target molecule analyte; and
   a plurality of molecules bound to the surface of the supporting material, other than the one or more target-specific capture probes, wherein each of the plurality of molecules comprises a first covalent bond-forming reactive group;
   a plurality of functionalized detectable label particles, wherein each of the plurality of functionalized detectable label particles comprises a plurality of molecules bound to the surface of a detectable label particle to provide a functionalized detectable label particle, wherein each of the plurality of molecules bound to the surface of the detectable label particle comprises a member of a specific binding pair; and
   a plurality of linker molecules wherein each linker molecule in the plurality of linker molecules is configured to non-covalently bind one of the plurality of molecules bound to the surface of one of the plurality of functionalized detectable label particles,
wherein each linker molecule comprises a plurality of second covalent bond-forming reactive groups, wherein the first covalent bond-forming reactive group is capable of forming a covalent bond with one of the second covalent bond-forming reactive groups, and wherein the plurality of functionalized detectable label particles do not have binding affinity for the target molecule analyte.

10. The reaction mixture of claim 9, further comprising the target molecule analyte specifically bound to one of the one or more target-specific capture probes.

11. The reaction mixture of claim 10, further comprising a label probe specifically bound to the target molecule analyte.

12. The reaction mixture of claim 11, further comprising an enzyme conjugate specifically bound to the label probe.

13. The reaction mixture of claim 12, wherein a functionalized detectable label particle of the plurality of functionalized detectable label particles is bound to multiple linker molecules of the plurality of linker molecules which are bound, via covalent bonds between the first covalent bond forming reactive groups and the second covalent bond forming reactive groups, to the surface of the supporting material, in proximity to the bound target molecule analyte.

14. The reaction mixture of claim 13, comprising a plurality of spatially separated, individually detectable target loci.

15. The reaction mixture of claim 13, wherein the target molecule-analyte is present in the reaction mixture at a concentration of less than about 100 fM.

16. The reaction mixture of claim 13, wherein the target molecule-analyte is present in the reaction mixture at a concentration of about 0.1 fM to about 100 fM.

17. The reaction mixture of claim 1, wherein the functionalized detectable label particles are functionalized magnetic beads.

18. The reaction mixture of claim 17, wherein the functionalized magnetic beads have a diameter of about 100 nm to about 1 μm.

19. The reaction mixture of claim 17, wherein the functionalized magnetic beads have a diameter of about 1 μm or greater.

20. The reaction mixture of claim 1, wherein each of the plurality of molecules bound to the surface of the supporting material is a synthetic, non-naturally occurring molecule.

21. The reaction mixture of claim 1, wherein the supporting material comprises silicon.

22. The reaction mixture of claim 20, wherein each of the synthetic, non-naturally occurring molecules comprises a dendrimer structure.

23. The reaction mixture of claim 20, wherein each of the synthetic, non-naturally occurring molecules comprises a tyrosine amino acid.

24. The reaction mixture of claim 20, wherein each of the synthetic, non-naturally occurring molecules comprises a phenol or phenol derivative copolymer.

25. The reaction mixture of claim 20, wherein each of the synthetic, non-naturally occurring molecules comprises lysine and tyrosine amino acids.

26. The reaction mixture of claim 20, wherein each of the synthetic, non-naturally occurring molecules comprises tyramine or a tyramine derivative.

27. The reaction mixture of claim 20, wherein each of the synthetic, non-naturally occurring molecules comprises thymine or a thymine derivative.

28. The reaction mixture of claim 9, wherein the functionalized detectable label particles are functionalized magnetic beads.

29. The reaction mixture of claim 9, wherein the supporting material comprises silicon.

30. The reaction mixture of claim 9, wherein each of the plurality of molecules bound to the surface of the supporting material is a synthetic, non-naturally occurring molecule.

31. The reaction mixture of claim 30, wherein each of the synthetic, non-naturally occurring molecules comprises a dendrimer structure.

32. The reaction mixture of claim 30, wherein each of the synthetic, non-naturally occurring molecules comprises a tyrosine amino acid.

33. The reaction mixture of claim 30, wherein each of the synthetic, non-naturally occurring molecules comprises a phenol or phenol derivative copolymer.

34. The reaction mixture of claim 30, wherein each of the synthetic, non-naturally occurring molecules comprises tyramine or a tyramine derivative.

35. The reaction mixture of claim 30 wherein each of the synthetic, non-naturally occurring molecules comprises thymine or a thymine derivative.

36. The reaction mixture of claim 1, wherein the supporting material comprises glass or plastic.

37. The reaction mixture of claim 9, wherein the supporting material comprises glass or plastic.

* * * * *